US009543694B2

(12) United States Patent
Tagawa

(10) Patent No.: US 9,543,694 B2
(45) Date of Patent: Jan. 10, 2017

(54) RADIATION IMAGING SYSTEM, RADIATION IMAGING APPARATUS, AND APPARATUS

(71) Applicant: CANON KABUSHIKI KAISHA, Tokyo (JP)

(72) Inventor: Motoki Tagawa, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 246 days.

(21) Appl. No.: 14/197,051

(22) Filed: Mar. 4, 2014

(65) Prior Publication Data

US 2014/0254756 A1 Sep. 11, 2014

(30) Foreign Application Priority Data

Mar. 6, 2013 (JP) ................................ 2013-044403

(51) Int. Cl.

*H05G 1/08* (2006.01)
*H01R 13/62* (2006.01)
*H04N 5/32* (2006.01)
*A61B 6/00* (2006.01)
*G01N 23/04* (2006.01)

(Continued)

(52) U.S. Cl.

CPC ............ *H01R 13/62* (2013.01); *A61B 6/4208* (2013.01); *A61B 6/4405* (2013.01); *H04N 5/32* (2013.01); *G01N 23/04* (2013.01); *H01R 13/6205* (2013.01); *H01R 13/6275* (2013.01); *H01R 24/28* (2013.01); *H01R 2107/00* (2013.01); *H01R 2201/12* (2013.01)

(58) Field of Classification Search

CPC ... H01R 13/62; H01R 13/6205; H01R 13/621; H01R 13/6215; H01R 13/622; H01R 13/623; H01R 13/625; H01R 13/627

USPC .... 378/91, 167, 170, 146, 101, 102; 439/39, 439/40

See application file for complete search history.

(56) References Cited

U.S. PATENT DOCUMENTS 6,231,349 B1 * 5/2001 Bullinger .......... H01R 13/7037 439/1
2003/0042418 A1 * 3/2003 Yamamoto ............ G03B 42/02 250/336.1

(Continued)

FOREIGN PATENT DOCUMENTS

JP 3610348 B2 1/2005
JP 3848288 B2 11/2006

(Continued)

*Primary Examiner* — Jason McCormack

(74) *Attorney, Agent, or Firm* — Canon USA, Inc. I.P. Division

(57) ABSTRACT

An X-ray imaging system includes an X-ray imaging apparatus for converting an X-ray into an image signal, a cable for transmitting signals to the X-ray imaging apparatus, a connector, disposed at an end of the cable, for connecting the cable and the X-ray imaging apparatus, and fixing portions for fixing the connector and the X-ray imaging apparatus and allowing the connector to be detached from the X-ray imaging apparatus by a detachment load. A cable outlet of the connector is separated from an outline center axis of the connector. The fixing portions include a first fixing portion disposed on the cable outlet side with respect to the connector outline center axis, and a second fixing portion disposed on the opposite side of the cable outlet. The moment of force required to detach the first fixing portion is larger than that required to detach the second fixing portion.

25 Claims, 20 Drawing Sheets

A B 200 300 232 S 222 130 N 120 150 100 260

(51) Int. Cl.

| | |
|---|---|
| *H01R 13/627* | (2006.01) |
| *H01R 24/28* | (2011.01) |
| *H01R 107/00* | (2006.01) |

(56) References Cited

U.S. PATENT DOCUMENTS

| | | | | |
|---|---|---|---|---|
| 2004/0198101 | A1* | 10/2004 | Rapp | H04N 5/2251 439/701 |
| 2009/0180595 | A1* | 7/2009 | Spahn | A61B 6/4233 378/197 |
| 2011/0189863 | A1* | 8/2011 | Sare | H01R 13/6205 439/39 |
| 2012/0282786 | A1* | 11/2012 | Neel | H01R 11/30 439/39 |
| 2014/0065846 | A1* | 3/2014 | Poh | H01R 11/30 439/39 |
| 2014/0113500 | A1* | 4/2014 | Goyal | H01L 31/05 439/698 |

FOREIGN PATENT DOCUMENTS

| | | | |
|---|---|---|---|
| JP | 2010-259680 | A | 11/2010 |
| KR | 10-2003-0019139 | A | 3/2003 |

* cited by examiner 300
201
2002 SECOND END
B
220
120
240
203
250
140
100
A
200
202
210
230
130
2001 FIRST END 300
2002
222
200
203 HOUSING
250
232
2001
255b GUIDE PIN
255a GUIDE PIN 150
200
2002
A'
S
N
232
120
260
222
S
N
B'
130
100
200
2001
300

250
1 Sout
2 Sin
3 Vcc
4 GND
5 GND
6 Vcc
7 Sin
8 Sout
250
8 Sout
7 Sin
6 Vcc
5 GND
4 GND
3 Vcc
2 Sin
1 Sout 250
1 Sout
2 Sin
3 Vcc
4 GND
5 (N. C.)
6 (N. C.)
7 (N. C.)
8 (N. C.)
250
8 (N. C.)
7 (N. C.)
6 (N. C.)
5 (N. C.)
4 GND
3 Vcc
2 Sin
1 Sout
101
140
Sout
Sin
Vcc
GND
GND
Vcc
Sin
Sout
107
GND
Vcc
Sin
Sout 101
107
GND
Vcc
S+
S−
140
S− S+ Vcc GND GND Vcc S+ S−
1 2 3 4 5 6 7 8
250
1 S−
2 S+
3 Vcc
4 GND
5 (N. C.)
6 (N. C.)
7 S+
8 S−
250
8 S−
7 S+
6 (N. C.)
5 (N. C.)
4 GND
3 Vcc
2 S+
1 S−

300
100
A
B
240
220
203
250
120
140
130
233
260
200

RADIATION IMAGING SYSTEM, RADIATION IMAGING APPARATUS, AND APPARATUS

BACKGROUND OF THE INVENTION

Field of the Invention

The present invention relates to a radiation imaging system having a detachable connector, a radiation imaging apparatus, and an apparatus including the connector.

Description of the Related Art

In recent years, apparatuses for capturing a digital image by using a semiconductor sensor have been increasingly used as an X-ray imaging apparatus for medical image diagnosis and non-destructive inspection. This allows, unlike conventional image acquisition using a photosensitive film, an obtained image to be instantaneously checked, improving the work efficiency. Further, such an apparatus has a very wide dynamic range, and therefore this also enables imaging to be performed without being affected by a change in the amount of X-ray exposure.

With the decrease in size and weight of the above-described apparatus, a portable type has been put into practical use (see Japanese Patent No. 3848288). The portable type X-ray imaging apparatus allows imaging of a subject having any posture, and is preferably used for X-ray imaging in general wards and outdoors. This portable type X-ray imaging apparatus may include a cable for supplying power from a power supply apparatus and/or transferring data to a control apparatus. Further, the X-ray imaging apparatus configured to detachably attach the cable thereto is discussed in Japanese Patent No. 3610348. An apparatus of this type can be operated with the cable disconnected when the apparatus does not require cable connection, for example, when the apparatus is stored or transported, so that the ease of handling is improved. Further, a technique for connecting the above-described cable to an X-ray imaging apparatus by using a magnetic attraction force is discussed in Japanese Patent Application Laid-Open No. 2010-259680.

If the cable connection using magnetic attraction is easily detached unintentionally, for example, by vibrations or the cable's own weight, the operability of the apparatus may be degraded. On the other hand, when the cable is intentionally detached, it is desirable that the cable can be easily detached with an appropriate force.

SUMMARY OF THE INVENTION

According to an aspect of the present invention, an X-ray imaging system includes an X-ray imaging apparatus for converting an X-ray into an image signal, a cable for at least one of transmitting/receiving electrical signals to/from the X-ray imaging apparatus and supplying power to the X-ray imaging apparatus, a connector, which is disposed at an end of the cable, for connecting the cable and the X-ray imaging apparatus, and fixing portions for fixing the connector and the X-ray imaging apparatus and allowing the connector to be detached from the X-ray imaging apparatus by a detachment load. A cable outlet of the connector is separated from an outline center axis of the connector. The fixing portions include a first fixing portion disposed on the cable outlet side with respect to the connector outline center axis, and a second fixing portion disposed on the opposite side of the cable outlet with respect to the connector outline center axis.

The moment of force required to detach the first fixing portion is larger than the moment of force required to detach the second fixing portion.

Further features of the present invention will become apparent from the following description of exemplary embodiments with reference to the attached drawings.

BRIEF DESCRIPTION OF THE DRAWINGS

FIG. 7A illustrates the connection surface on the radiation imaging apparatus side. FIG. 7B is a sectional view illustrating the connection surface on the radiation imaging apparatus side. FIG. 7C illustrates the connection surface on the cable side.

FIG. 9A illustrates pin assignments according to an exemplary embodiment. FIG. 9B illustrates pin assignments according to another exemplary embodiment. FIG. 9C illustrates pin assignments for using differential communication signals. FIG. 9D illustrates pin assignments with reduced number of pins. FIG. 9E illustrates polarity reversal of a signal.

FIG. 11A illustrates a case where the radiation imaging apparatus is horizontally placed. FIG. 11B illustrates a case where the radiation imaging apparatus is vertically placed.

DESCRIPTION OF THE EMBODIMENTS

Figure 1:
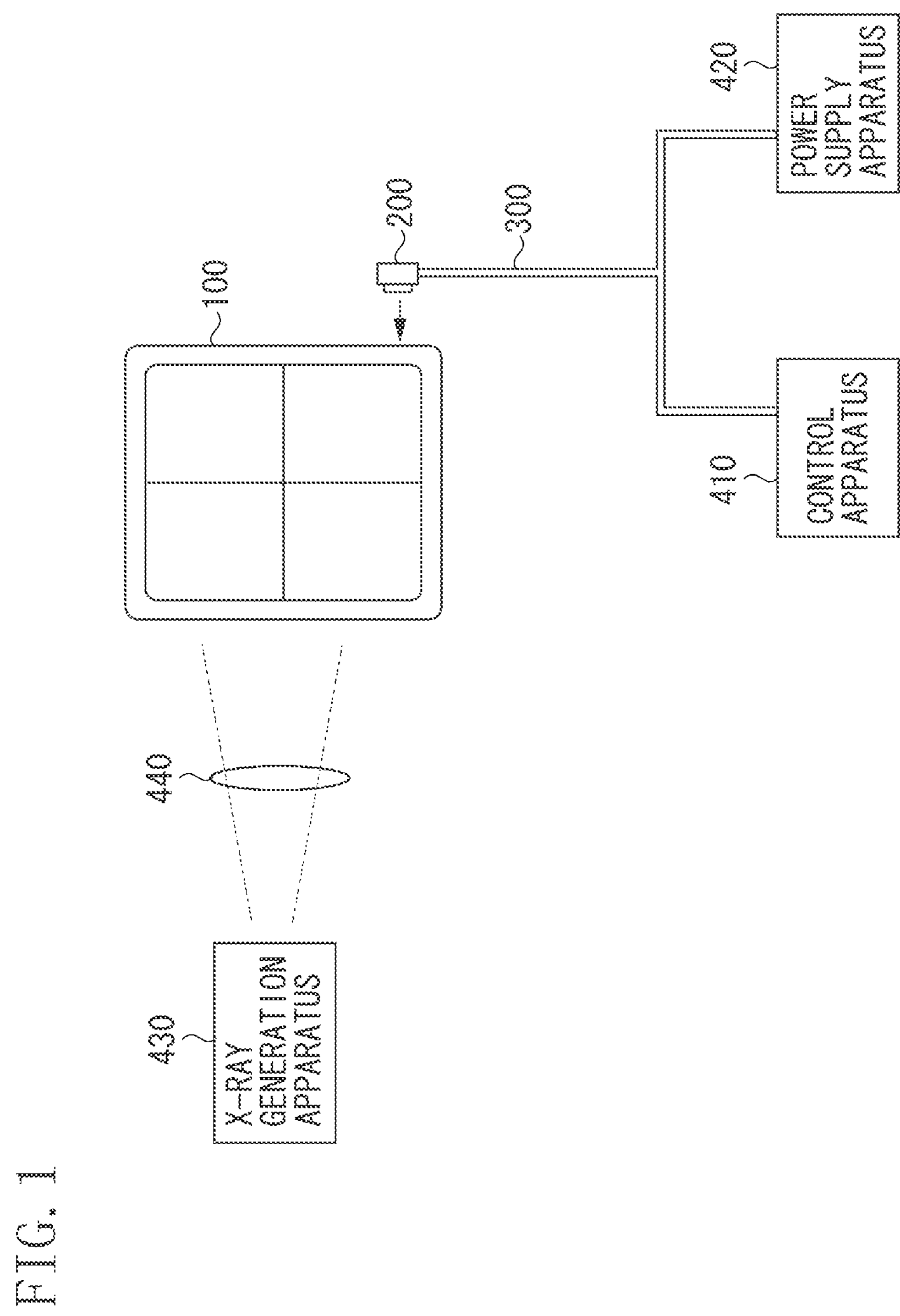
FIG. 1 illustrates a configuration of a radiation imaging system according to an exemplary embodiment of the present invention.

The configuration of a radiation imaging system according to an exemplary embodiment will be described below with reference to FIG. 1. The radiation imaging system according to an exemplary embodiment includes a radiation imaging apparatus 100, and a connector 200 detachably attached to the radiation imaging apparatus 100. The radiation imaging apparatus 100 detects radiation that has been generated by an X-ray generation apparatus 430 (a radiation generation apparatus) and has transmitted through a subject 440 and reads the detected radiation values to generate radiation image data. The connector 200 provides the radiation imaging apparatus 100 with a communication path for communicating with a control apparatus 410 and/or with power from a power supply apparatus 420. The connector 200 is fixed to an end portion of a cable 300. The connector 200 enables the radiation imaging apparatus 100 to be electrically and physically connected to an external apparatus, such as the control apparatus 410 and the power supply apparatus 420, via the cable 300.

Electrical connection portions are formed on the radiation imaging apparatus 100 and the connector 200 to provide at least one of the above-described communication path and power. To fix the electrical connection portions, two fixing portions are formed: a first fixing portion where a predetermined fixing force is mutually produced between the radiation imaging apparatus 100 and a first area of the connector 200, and a second fixing portion where a fixing force larger than the above-described predetermined fixing force is mutually produced between the radiation imaging apparatus 100 and a second area of the connector 200. This configuration enables the connector 200 to be easily detached by applying a force to the connector 200 near the first area where a small fixing force is exerted. More specifically, if a position for detaching the connector 200 is predetermined, detaching the connector 200 in a position other than the predetermined position requires a larger force, thereby reducing the possibility of the connector 200 being unintentionally detached.

The radiation imaging apparatus 100 is, for example, a portable type radiation imaging apparatus including a radiation sensor having an approximately rectangular-shaped detection surface in an approximately cuboid-shaped housing. The radiation imaging apparatus 100 further includes a connection portion for connection with the connector 200 and a wireless communication circuit, and is capable of wiredly and wirelessly communicating with an external apparatus. The radiation imaging apparatus 100 according to an exemplary embodiment is driven according to the control signal from the control apparatus 410. Image information obtained by the radiation imaging apparatus 100 is transmitted to the control apparatus 410, and is subjected to various image processing and display processing.

The connector 200 is a detachable connector which is fixedly connected to an end of the cable 300 for providing the radiation imaging apparatus 100 (the partner apparatus) with at least one of the power from the power supply apparatus 420 and the communication path for communicating with the control apparatus 410.

The control apparatus 410 is an image display terminal including a communication circuit for transmitting to the radiation imaging apparatus 100 control signals, for example, for instructing the radiation imaging apparatus 100 to perform power control and sensor drive control and for receiving radiation image data from the radiation imaging apparatus 100, an image processing circuit for performing image processing on the received radiation image data, and a display control unit for displaying the processed image data on a display unit.

The power supply apparatus 420 supplies power to the radiation imaging apparatus 100. The cable 300 includes signal lines for transmitting the above-described control signals and image information, and power supply lines for supplying the above-described power. The cable 300 is connected between the radiation imaging apparatus 100 and the control apparatus 410, and between the radiation imaging apparatus 100 and the power supply apparatus 420. The cable 300 according to an exemplary embodiment may be connected to either the control apparatus 410 or the power supply apparatus 420.

Figure 2:
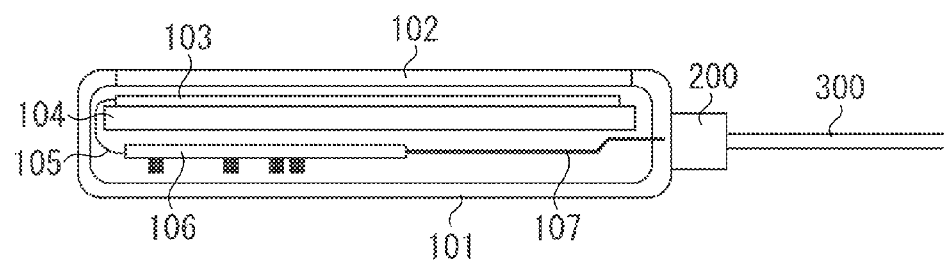
FIG. 2 is a sectional view illustrating a radiation imaging apparatus according to an exemplary embodiment.

The radiation imaging apparatus 100 according to an exemplary embodiment will be described below with reference to FIG. 2. FIG. 2 is a sectional view illustrating the radiation imaging apparatus 100 according to an exemplary embodiment. Radiation is incident from above the view. The radiation imaging apparatus 100 is connected to the connector 200 on the side surface portion of a housing 101. The radiation imaging apparatus 100 may be connected to the connector 200 on the incidence surface or the rear surface of the housing 101. However, when the radiation imaging apparatus 100 is used, since arranging the connector 200 on the side surface portion of the housing 101 does not form a projection on the incidence surface or the rear surface of the housing 101, burdens on the subject 440 are reduced. The housing 101 of the radiation imaging apparatus 100 is made of such materials as aluminum, magnesium, and carbon fiber reinforced plastic (CFRP). Use of such materials provides a sufficient mechanical strength for supporting the subject 440 during the imaging and for withstanding a fall by carelessness, and can also save weight to reduce burdens during the transportation. An X-ray transmitting plate 102 made of CFRP and the like is disposed on the X-ray incidence surface side. The radiation imaging apparatus 100 includes an X-ray sensor panel (radiation sensor) 103 formed of photoelectric conversion elements and phosphors laminated on a glass substrate. When the X-ray sensor panel 103 is irradiated with an X-ray, the phosphors emit light and the photoelectric conversion elements convert the light into an electrical signal to generate an image signal. The X-ray sensor panel 103 is provided with a rigid supporting member 104 bonded to the opposite side surface of the X-ray incidence surface so that distortion or cracking does not occur due to an external load or vibrations during the transportation. Further, the X-ray sensor panel 103 is connected to an electrical circuit board 106 fixed to the supporting member 104 via a flexible substrate 105. Signals and the like transmitted through the cable 300 are connected to the electrical circuit board 106 via wiring 107 included in the radiation imaging apparatus 100. The electrical circuit board 106 controls the X-ray sensor panel 103 and processes image signals. If the cable 300 is not connected to the power supply apparatus 420, or if external power supply is stopped because of a problem in internal processing of the radiation imaging apparatus 100, a battery provided in the radiation imaging apparatus 100 supplies power to each unit.

The electrical circuit board 106 according to an exemplary embodiment includes a wireless communication circuit for wirelessly exchanging control signals and image signals, a wired communication circuit for controlling communication performed via the connection portion connecting to the connector 200, a drive circuit for driving the X-ray sensor panel 103, a reading circuit for amplifying an electrical signal output by the drive circuit, and performing AD conversion on the electrical signal, a memory for storing read image data, an image processing circuit for processing the read image data, and a voltage control circuit for supplying power from the battery or the power supply apparatus 420 to each unit. An electrical circuit board 106 according to another exemplary embodiment further includes a micro processing unit (MPU) for totally controlling these circuits, a storage unit for storing a program for executing the above-described imaging control, and a working memory for loading the program.

The connection portion between the radiation imaging apparatus 100 and the connector 200 according to an exemplary embodiment will be described below with reference to FIG. 3. The connection portion of the radiation imaging apparatus 100 include first and second apparatus-side fixing members 130 and 120, and a plurality of apparatus-side connection terminals 140 between the fixing members 130 and 120, which are all disposed on the outside surface of the housing 101. The second apparatus-side fixing member 120 has a larger area than the first apparatus-side fixing member 130 on the outside surface of the housing 101. The connector 200 is provided with first and second connector-side fixing members 230 and 220 that are disposed along the contact surface for contact with the radiation imaging apparatus 100. The second connector-side fixing member 220 has a larger area than the first connector-side fixing member 230 on the contact surface of the connector 200. A plurality of connector-side connection terminals 250 and an outer wall portion 203 surrounding the peripheral edge portion of the connection terminals 250 are disposed between the first and second connector-side fixing members 230 and 220. The first and second connector-side fixing members 230 and 220, the connector-side connection terminals 250, and the outer wall portion 203 are fixed to a housing 210 of the connector 200 (hereinafter referred to as the connector housing 210).

Forces are mutually exerted between the first connector-side fixing member 230 and the first apparatus-side fixing member 130 and between the second connector-side fixing member 220 and the second apparatus-side fixing member 120, so that the connector 200 is fixed to the radiation imaging apparatus 100. Fixing the first fixing members 230 and 130 and fixing the second fixing members 220 and 120 cause the connection terminals 250 and 140 to come into contact with each other, thereby establishing the communication path and the power supply path. The outer wall portion 203 is inserted into a hole portion provided between the first and second apparatus-side fixing members 130 and 120 and the connection terminals 140 to prevent the connector 200 from moving in the direction along the side surface of the radiation imaging apparatus 100. Thus, in a state where the connector 200 is attached to the radiation imaging apparatus 100 by the first fixing members 230 and 130 and the second fixing members 220 and 120, when a force larger than the fixing force is applied to the connector 200 in a direction away from the radiation imaging apparatus 100, the connector 200 becomes detached from the radiation imaging apparatus 100.

Figure 3:
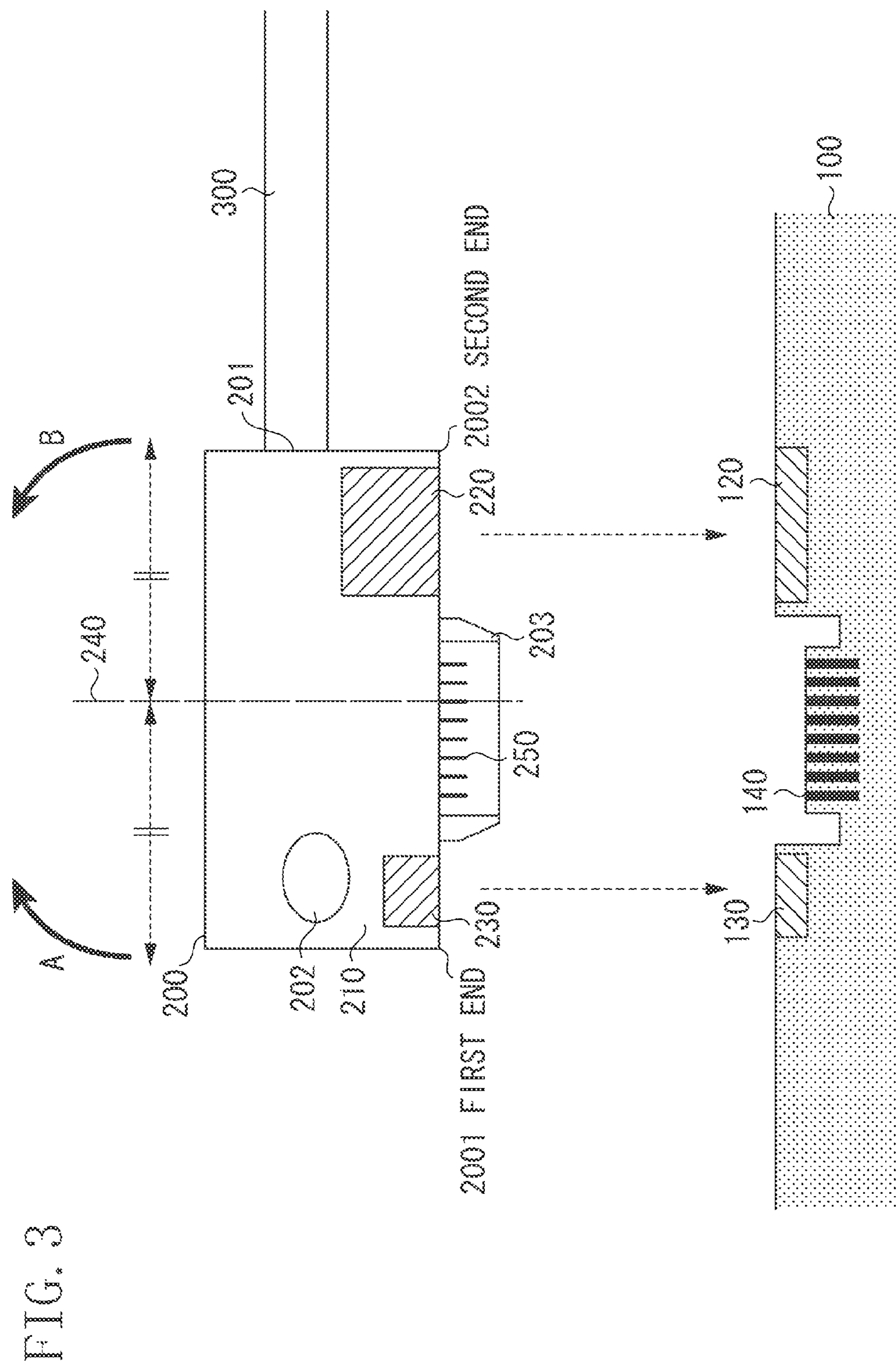
FIG. 3 illustrates a connection portion between a radiation imaging apparatus and a connector according to an exemplary embodiment.

Here, the fixing force exerted between the second apparatus-side fixing member 120 and the second connector-side fixing member 220 is made larger than the fixing force exerted between the first apparatus-side fixing member 130 and the first connector-side fixing members 230, so that the force required to detach the connector 200 is different between when the connector 200 is pulled up from the first connector-side fixing member 230 side in the direction A illustrated in FIG. 3 and when the connector 200 is pulled up from the second connector-side fixing member 220 side in the direction B illustrated in FIG. 3. This configuration will be described in detail below.

When the connector 200 is pulled up in the direction A illustrated in FIG. 3, the moment around the vicinity of a second end 2002 will act on the connector 200. In this case, the moment in the direction for moving the connector 200 toward the radiation imaging apparatus 100 side is produced by the first and second connector-side fixing members 230 and 220, ignoring the influence of frictions at the outer wall portion 203 and between the connection terminals 140 and 250. Since the second connector-side fixing member 220 is close enough to the second end 2002, the moment is largely influenced mainly by the first connector-side fixing member 230. Conversely, when the connector 200 is pulled up in the direction B illustrated in FIG. 3, the moment around the vicinity of a first end 2001 acts on the connector 200. In this case, for a similar reason to the above, the moment is largely influenced mainly by the second connector-side fixing member 220. Thus, the connector 200 is configured such that the magnitude of the moment exerted by the first and second connector-side fixing members 230 and 220 on the first end 2001 is different from that on the second end 2002. Since the fixing force of the second connector-side fixing member 220 is larger than that of the first connector-side fixing member 230, pulling up the connector 200 in the direction B illustrated in FIG. 3 requires a larger force (moment) than pulling it up in the direction A illustrated in FIG. 3. This makes it easier to detach the connector 200 by pulling it up in the direction A illustrated in FIG. 3, while making it relatively difficult to detach the connector 200 by pulling it up in the direction B illustrated in FIG. 3. Referring to the example illustrated in FIG. 3, this principle is similar to the fact that the magnitude of the moment around a center axis 240 of the connector 200 (hereinafter referred to as the connector outline center axis 240) exerted by the second fixing members 120 and 220 is larger than that exerted by the first fixing members 130 and 230.

Here, a recessed portion 202 is provided near the first connector-side fixing member 230 or the first end 2001. The recessed portion 202 is provided at least in a position closer to the first end 2001 than to the second end 2002. The recessed portion 202 is provided on each of the two opposing surfaces of the connector 200. The two recessed portions 202 form a holding portion of the connector 200. This holding portion makes it easier for an operator to hold the connector 200, and can guide the operator to apply a force in the direction A illustrated in FIG. 3.

Here, the cable 300 enters the connector 200 from a cable outlet 201 provided on the connector housing 210, and is directly or indirectly connected to the connection terminals 250. The cable outlet 201 is disposed near the second connector-side fixing member 220 or the second end 2002, i.e., at least in a position closer to the second end 2002 than to the first end 2001. This prevents, even if a large force applied to the cable 300 exerts a force in the direction B illustrated in FIG. 3, the connector 200 from being detached at least as long as the applied force (moment) does not exceed the force required to detach the connection 200 by pulling it up in the direction A illustrated in FIG. 3. Thus, it becomes easier to intentionally detach the connector 200 by using the holding portion while it becomes more difficult that the connector 200 is unintentionally detached, for example, due to a load applied on the cable 300.

Each of the connection terminals 250 of the connector 200 is connected to each electrical wire of the cable 300 inside the connector 200. The cable 300 is retained by using a clamp member inside the connector 200 as required to prevent the cable 300 from being disconnected, and is taken out from the cable outlet 201 to the outside of the connector 200. The X-ray imaging apparatus 100 has the connection terminals 140 at a position corresponding to the connection terminals 250 of the connector 200. When the connector 200 is fixed to the radiation imaging apparatus 100, the cable 300 and the radiation imaging apparatus 100 are connected to each other via the connection terminals 250 and 140. It is desirable that the cable 300 is taken out approximately horizontally with respect to the connector connection surface of the radiation imaging apparatus 100. This prevents the outer shape of the radiation imaging apparatus 100 with the connector 200 attached thereto from becoming too large, facilitating the handling of the radiation imaging apparatus 100 when storing it into various storage racks.

Figure 4:
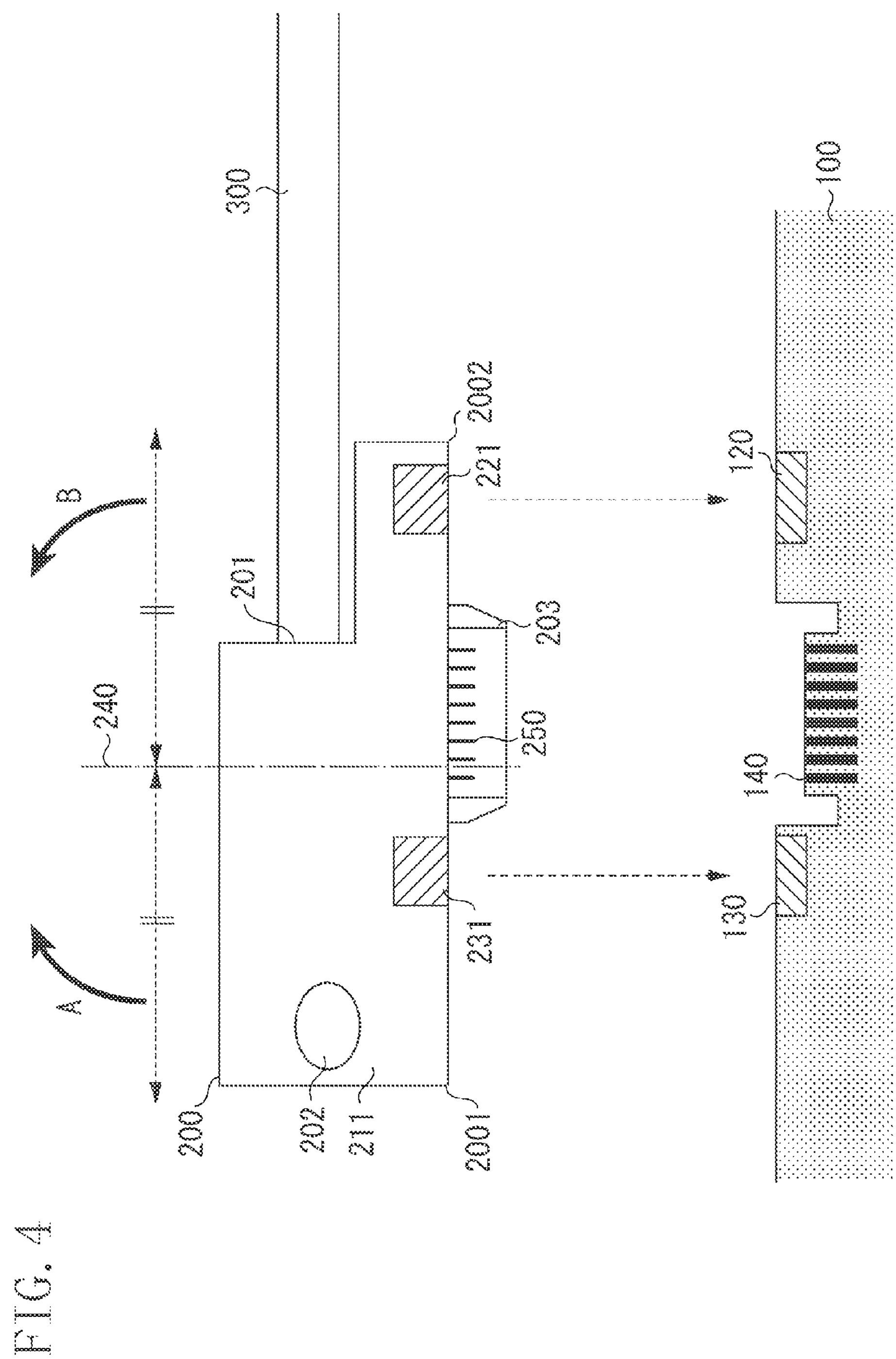
FIG. 4 illustrates a connection portion between a radiation imaging apparatus and a connector according to another exemplary embodiment.

A connection portion between a radiation imaging apparatus 100 and a connector 200 according to another exemplary embodiment will be described with reference to FIG. 4. An example illustrated in FIG. 4 achieves the function equivalent to that in the above-described example by arranging first and second connector-side fixing members 231 and 221 with respect to a connector housing 211 differently from the example illustrated in FIG. 3. In the example illustrated in FIG. 4, the first and second connector-side fixing members 231 and 221 have approximately the same shape, and respective forces acting on the first and second connector-side fixing members 231 and 221 have approximately the same magnitude. Unlike the example illustrated in FIG. 3, the first and second apparatus-side fixing members 130 and 120 have approximately the same size. Note that the term "approximately the same" indicates that, for example, a manufacturing error or an error of several percent can be ignored, and relevant shapes or sizes can be recognized as identical. Here, the distance between the first connector-side fixing member 231 (or the center position of the contact surface thereof) and the first end 2001 is larger than the distance between the second connector-side fixing member 221 (or the center position of the contact surface thereof) and the second end 2002. Thus, the magnitude of the moment exerted by the first and second fixing members 231 and 221 on the first end 2001 is larger than that on the second end 2002. Therefore, the magnitude of the force (moment) required to detach the connector 200 in the direction A illustrated in FIG. 4 is smaller than the magnitude of the force (moment) required to detach it in the direction B illustrated in FIG. 4. This makes it easier to detach the connector 200 by using the recessed portion 202, while making it more difficult that the connector 200 becomes detached by a load on the cable 300. To achieve such an arrangement, the connector housing 211 has a structure in which the area of the top surface is smaller than that of the contact surface, and the outlet 201 of the cable 300 is disposed in a position closer to the connector outline center axis 240 or the first end 2001. Thus, the first and second connector-side fixing members 231 and 221 can be made of the same material, providing advantages in terms of parts management and cost. Disposing the outlet 201 of the cable 300 closer to the first end 2001 enables suppression of the magnitude of the moment exerted by a load on the cable 300, ensuring a sufficient force for retaining the connection without increasing the attraction force of the magnet 221 and the attraction plate 120 too much.

On the other hand, the example illustrated in FIG. 3 has an advantage that the connector shape can be simplified. In another example, the examples illustrated in FIGS. 3 and 4 can be suitably partly employed, i.e., the above-described fixing members having suitable sizes can be suitably disposed.

Figure 5:
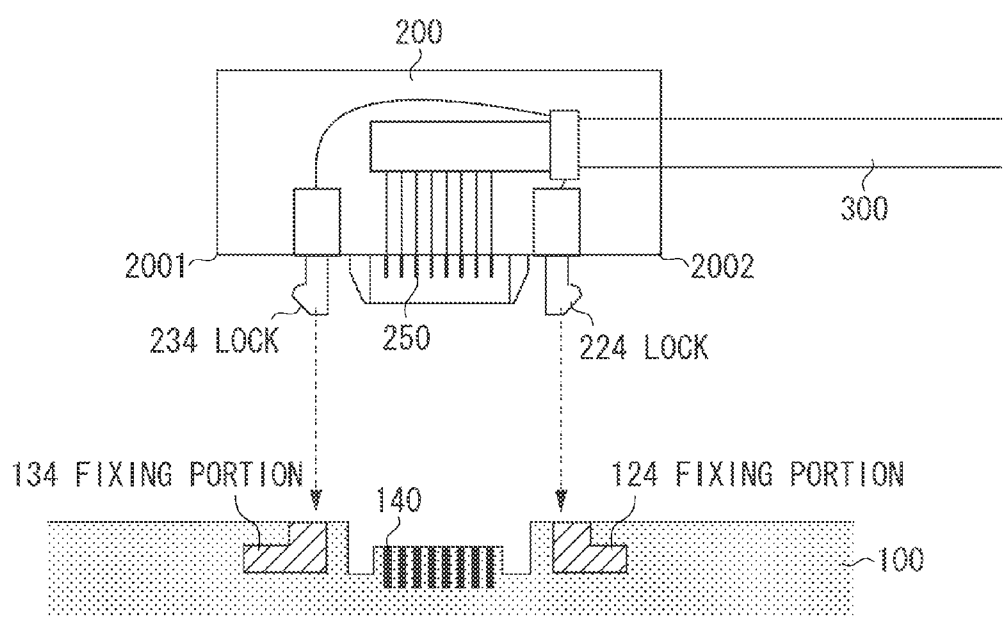
FIG. 5 illustrates a connection portion between a radiation imaging apparatus and a connector according to yet another exemplary embodiment.

A connection portion between a radiation imaging apparatus 100 and a connector 200 according to yet another exemplary embodiment will be described below with reference to FIG. 5. In this example, the connector 200 has two L-shaped fixing members, a first lock 234 and a second lock 224, as connector-side fixing members. Each of the first and second locks 234 and 224 is formed of a protruding member protruding outward from the contact surface of the connector 200 and a portion further protruding from the leading end of the protruding member in the direction along the contact surface (in the horizontal direction). The horizontal protruding portions of the first and second locks 234 and 224 are oriented at least in the opposite directions. As mating fixing members, the radiation imaging apparatus 100 has first and second fixing members 134 and 124 each having an L-shaped recessed portion. The horizontal protruding member of the first lock 234 is larger than that of the second lock 224. The first and second locks 234 and 224 are made of a deformable material, such as resin. The first and second locks 234 and 224 are inserted into the fixing members 134 and 124, respectively, while deforming to fit into the respective L-shaped recessed portions of the fixing members 134 and 124, so that the first and second fixing portions are configured. In the fixed state, the first and second locks 234 and 224 do not deform at all, or deform less than while being inserted. Since the protruding portion of the first lock 234 is larger than that of the second lock 224, detaching the connector 200 from the cable side requires a large force (moment) because of the deformation and friction of the first lock 234.

Figure 6:
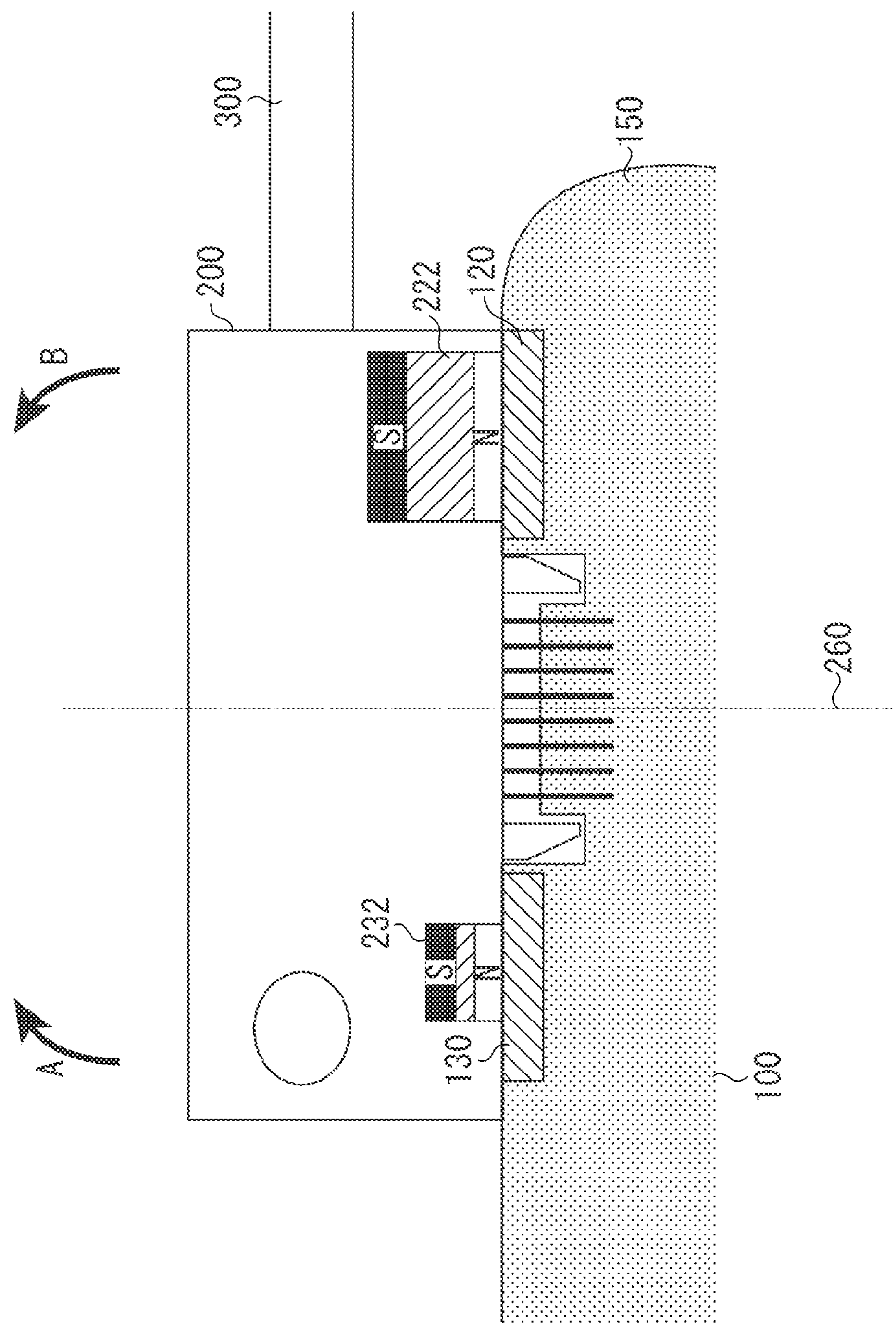
FIG. 6 illustrates a connection portion between a radiation imaging apparatus and a connector according to yet another exemplary embodiment.

A connection portion between a radiation imaging apparatus 100 and a connector 200 according to yet another exemplary embodiment will be described below with reference to FIG. 6.

Various types of apparatus-side and connector-side fixing members can be employed. For example, using magnets on one side and magnetic materials on the other side enables the connector 200 to be attached to the radiation imaging apparatus 100 by magnetism. The magnets may be a magnetized material or an electromagnet. When an electromagnet is used, it operates as a magnet by receiving power supply from the power supply apparatus 420 or the battery. When a magnet is used, increasing the volume or contact surface area of the magnet allows adjustment of the magnitude of magnetism acting between the apparatus-side and connector-side fixing members. In this case, for example, magnets are used as the connector-side fixing members, and attraction plates made of a magnetic material are used as the apparatus-side fixing members. Magnets and attraction plates may be used reversely, or magnets may be used as both the connector-side and apparatus-side fixing members.

The connector 200 includes magnets 222 and 232. The connection portion of the radiation imaging apparatus 100 members includes attraction plates 120 and 130 in positions facing the magnets 222 and 232, respectively. The connector 200 is fixed to the radiation imaging apparatus 100 by the attraction force between the magnet 222 and the attraction plate 120 and the attraction force between the magnet 232 and the attraction plate 130. The connector 200 is fixed only by the magnetic attraction force. Therefore, if an overload is applied, for example, if the operator's foot is caught by the cable 300, the connector 200 can be detached from the radiation imaging apparatus 100, preventing damage to the radiation imaging apparatus 100, the connector 200, and the cable 300.

Here, the attraction force between the magnet 222 and the attraction plate 120 is set to be larger than the attraction force between the magnet 232 and the attraction plate 130. This is achieved, for example, by using the magnets 222 and 232 having different sizes and materials. Thus, detaching the connector 200 in the direction B illustrated in FIG. 6 requires a larger moment of force than detaching the connector 200 in the direction A illustrated in FIG. 6. Further, the cable outlet 201 is disposed on the side closer to the magnet 222 than a connector outline center axis 260. Thus, when the cable 300 is pulled, detaching the connector 200 requires the force in the direction B illustrated in FIG. 6. The above-described configuration ensures a sufficient force for retaining the connection (in the direction B) when the cable 300 is pulled, and allows the connector 200 to be easily detached by applying a force in the direction A without requiring a large force for detaching the connector 200, so that a radiation imaging system having favorable operability can be achieved. Further, providing a concave recessed portion 202 on the side closer to the magnet 232 than to the connector outline center axis 260 allows the operator to be guided to apply a force in the direction A when detaching the connector 200.

Here, the magnet 232 serving as the first connector-side fixing member and the magnet 222 serving as the second connector-side fixing member are disposed with the same polarities oriented in the same directions. In the example illustrated in FIG. 6, the magnets 232 and 222 (the first and second connector-side fixing members) are disposed such that both the north poles of the magnets 232 and 222 face the contact surface. If the connector 200 can be attached in either direction, and if the connector 200 attached in one direction for a long time causes the attraction plates 130 and 120 to be magnetized, attaching the connector 200 in the reverse direction may cause a failure to fix the connector 200 due to generation of a repulsive force. The above-described configuration can reduce the possibility of the failure.

In addition, when magnets are used, the influence of damage to the magnets can be reduced by providing a magnet protective member on the contact surface to cause the radiation imaging apparatus 100 and the connector 200 to exert a force on each other via the magnet protective member.

The configuration in the vicinity of the connection surfaces of the radiation imaging apparatus 100 and the connector 200 according to an exemplary embodiment will be described below with reference to FIGS. 7A, 7B, and 7C.

Figure 7A:
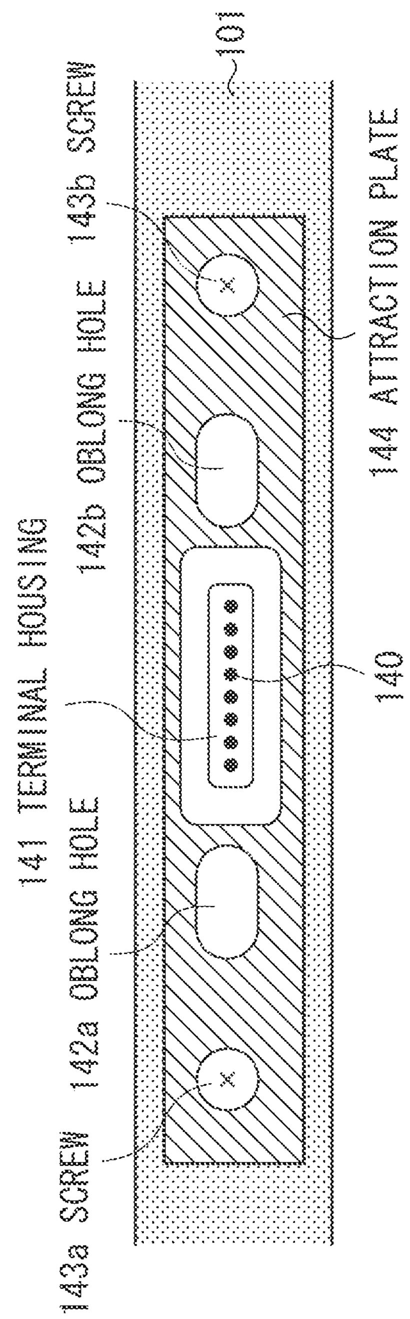
FIGS. 7A, 7B, and 7C illustrate connection surfaces of a radiation imaging apparatus and a connector according to an exemplary embodiment.
Figure 7B:
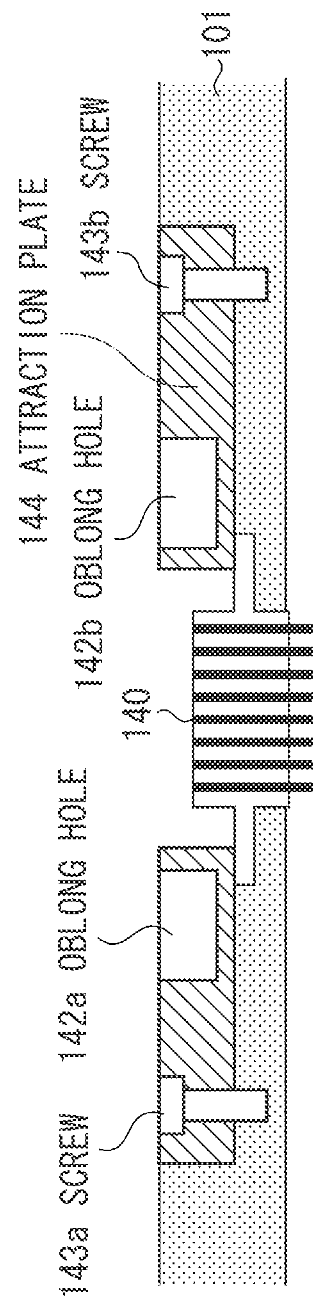

FIG. 7A illustrates a connection portion of the radiation imaging apparatus 100. FIG. 7B is a sectional view illustrating the connection surface on the radiation imaging apparatus 100 side. The connection portion is configured to include an attraction plate 144, apparatus-side connection terminals 140, and a terminal housing 141. The attraction plate 144, which is a plate member, and magnets serving as connector-side fixing members exert a magnetic force on each other to fix the fixing portions. The attraction plate 144 is a member made of a magnetic material, and is fixed to the side surface of the housing 101 with screws 143*a* and 143*b*. The attraction plate 144 includes two screw holes for the screws 143*a* and 143*b*, two oblong holes 142*a* and 142*b* for guide pins of the connector 200, and a hole portion for exposing the connection terminals 140 and the terminal housing 141 and for allowing passage of the connection terminal 250, which are all disposed in a line from the outside. Since the attraction plate 144 is subjected to magnetic force, the housing 101 is made of a nonmagnetic material, such as magnesium. The terminal housing 141 is an opening in which the outer wall portion 203 is disposed when the connector 200 is attached.

As illustrated in FIG. 7A, the connection portion of the radiation imaging apparatus 100 is disposed in point symmetry with respect to the connection terminals 140, allowing reverse connection of the connector 200 (described below).

Figure 7C:
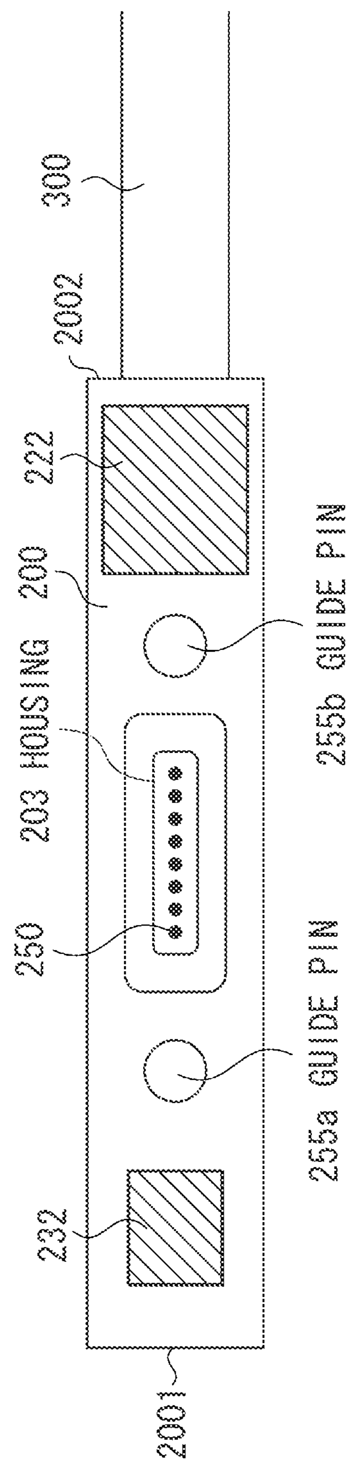

FIG. 7C illustrates the contact surface of the connector 200. The contact surface of the connector 200 includes the first and second fixing members 232 and 222, first and second guide pins 255*a* and 255*b*, the outer wall portion (housing) 203, and the connector-side connection terminals 250, which are all disposed in a line from the outside between the two longitudinal ends, the first end 2001 and the second end 2002.

The guide pins 255*a* and 255*b* are protruding members made of a high-stiffness material, such as a metal, and are inserted into the oblong holes 142*a* and 142*b* of the radiation imaging apparatus 100. This configuration can prevent the connector 200 from bidirectionally moving along the contact surface. Each of the oblong holes 142*a* and 142*b* has an approximately elliptic shape, and the diameter in the (long-side) direction along the side surface of the housing 101 of the radiation imaging apparatus 100 is larger than the diameter in the short-side direction of the side surface of the housing 101. This configuration makes the guide pins 255*a* and 255*b* easy to move in the long-side direction, and difficult to move in the short-side direction. Thus, it is easy to attach and detach the connector 200 to and from the radiation imaging apparatus 100 with the respective contact surfaces facing each other in the direction in which the guide pins 255*a* and 255*b* are easy to move. On the other hand, the guide pins 255*a* and 255*b* restrict the movement for inclining the connector 200 toward the incidence surface side or the rear surface side of the radiation imaging apparatus 100, thereby reducing the possibility of the connector 200 being unintentionally detached.

Examples of attachment forms of the connector 200 will be described below with reference to FIGS. 8A and 8B. The connector 200 is attached to the radiation imaging apparatus 100 either in a first attachment form or in a second attachment form which reverses the orientation of the connector 200 in the first attachment form. These attachment forms are achieved by the first and second connector-side fixing members 232 and 222, first and second areas 130 and 120 of the apparatus-side fixing members, and the connection terminals 250 and 140.

Figure 8A:
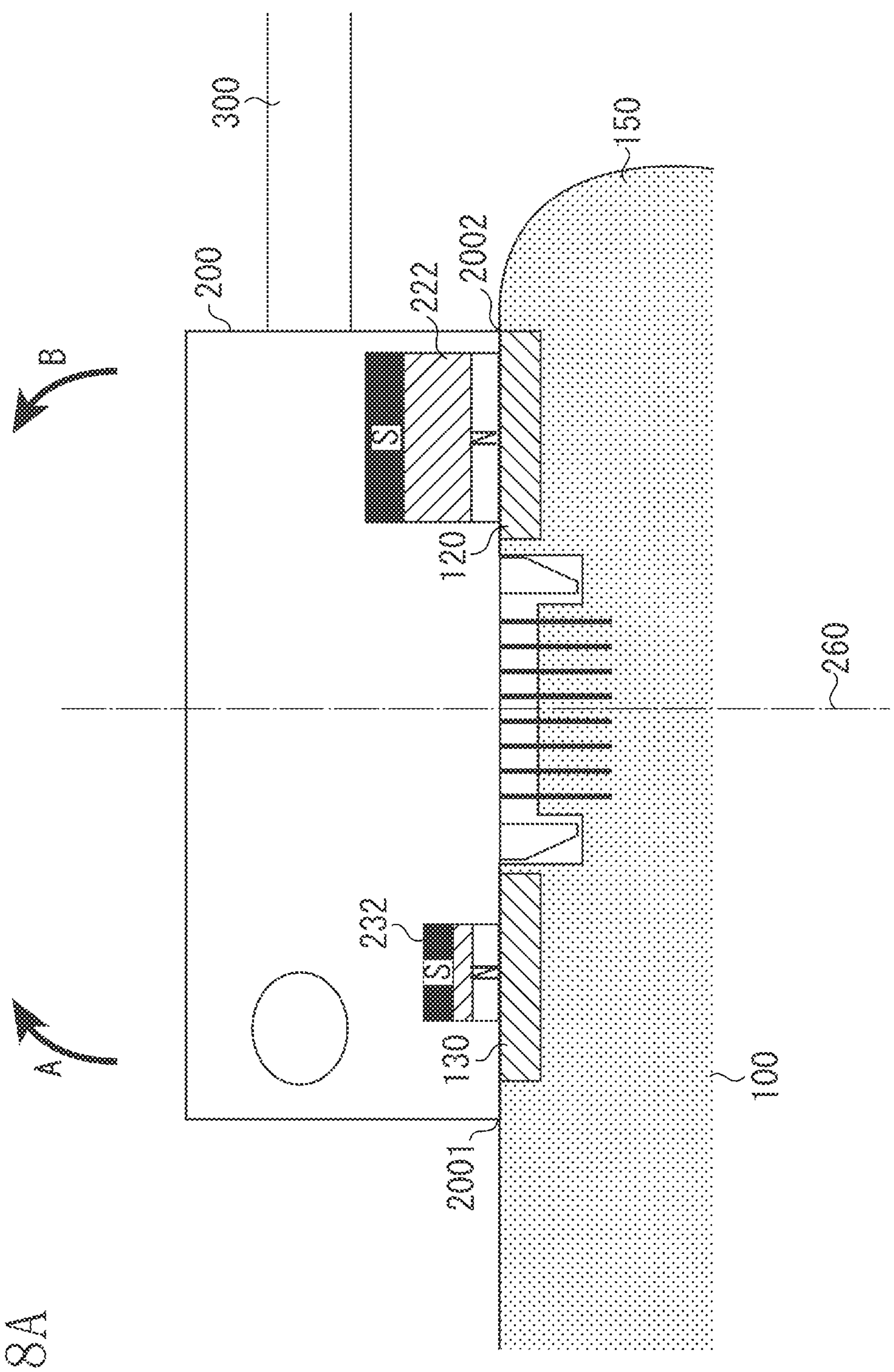
FIGS. 8A and 8B illustrate two attachment forms for attaching a radiation imaging apparatus and a connector according to an exemplary embodiment.

FIG. 8A illustrates the first attachment form in which the cable outlet 201 is outwardly oriented. FIG. 8B illustrates the second attachment form in which the cable outlet 201 is inwardly oriented by rotating the connector 200 in the first attachment form by 180 degrees. The fitting portion of the connector 200 has a shape that allows the connector 200 to be attached in either attachment form. With the configuration in symmetry with respect to the connection terminal center 260, in whichever orientation the connector 200 is attached, transfer of signals or supply of power by using the connection terminals 250 and 140 are electrically enabled. The asymmetry of the moment of force for detaching the connector 200 as illustrated in the above-described exemplary embodiments is due to the attraction forces and arrangements of the magnets 232 and 222 included in the connector 200. The attraction plates 130 and 120 of the radiation imaging apparatus 100 are arranged in symmetry with respect to the connection terminal center 260. This configuration can provide the first and second attachment forms. In the first attachment form, a fixing force is produced by a pair of the first connector-side fixing member 232 and the first area 130 of the first apparatus-side fixing member, and a fixing force is produced by a pair of the second connector-side fixing member 222 and the second area 120 of the second apparatus-side fixing member to connect the connector-side connection terminals 250 and the apparatus-side connection terminals 140. In the second attachment form, a fixing force is produced by a pair of the first connector-side fixing member 232 and the second area 120, and a fixing force is produced by a pair of the second connector-side fixing member 222 and the first area 130 to connect the connector-side connection terminals 250 and the apparatus-side connection terminals 140.

Figure 8B:
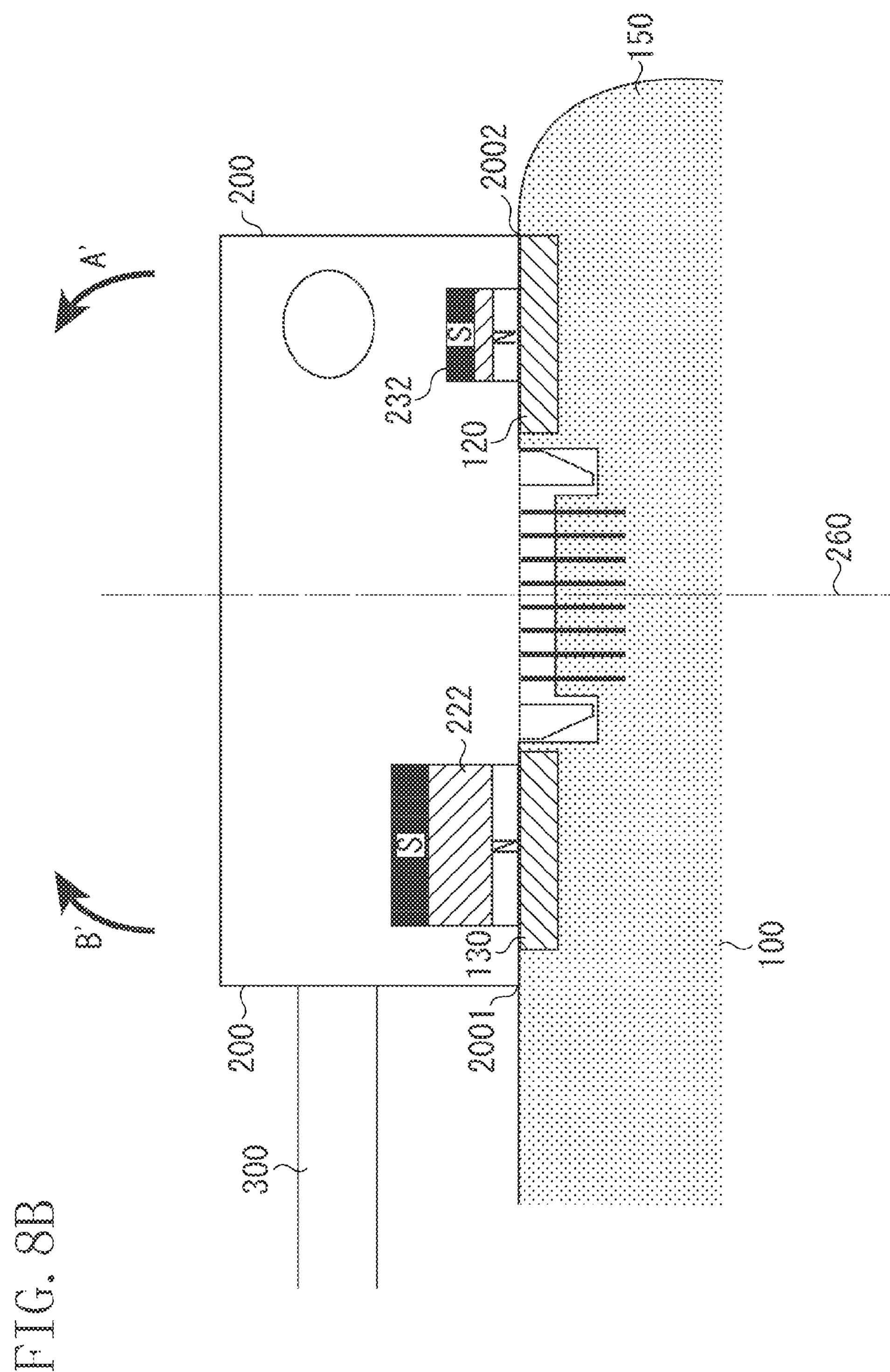

The moment of force for detaching the connector 200 in the direction A illustrated in FIG. 8A is the same as the moment of force for detaching it in the direction A' illustrated in FIG. 8B. Similarly, the moment of force for detaching the connector 200 in the direction B illustrated in FIG. 8A is the same as the moment of force for detaching it in the direction B' illustrated in FIG. 8B. Specifically, the sum of the magnitudes of the moment exerted on the connector 200 by the first and second connector-side fixing members is substantially identical in the first and second attachment forms. Thus, in whichever orientation the connector 200 is attached, an improved operational feeling as illustrated in the above-described exemplary embodiments can be obtained. Further, in whichever orientation the connector 200 is attached, the contact surface where the radiation imaging apparatus 100 and the connector 200 are in contact with each other does not overlap a corner round shape 150 of the radiation imaging apparatus 100 so that the connector 200 is stably attached to the radiation imaging apparatus 100.

Figure 9B:
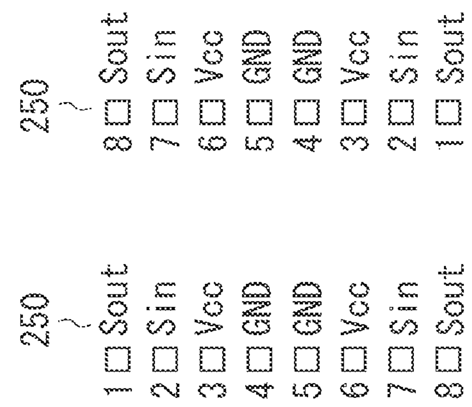
FIGS. 9A, 9B, 9C, 9D, 9E, and 9F illustrate signals flowing through connection terminals.
Figure 9A:
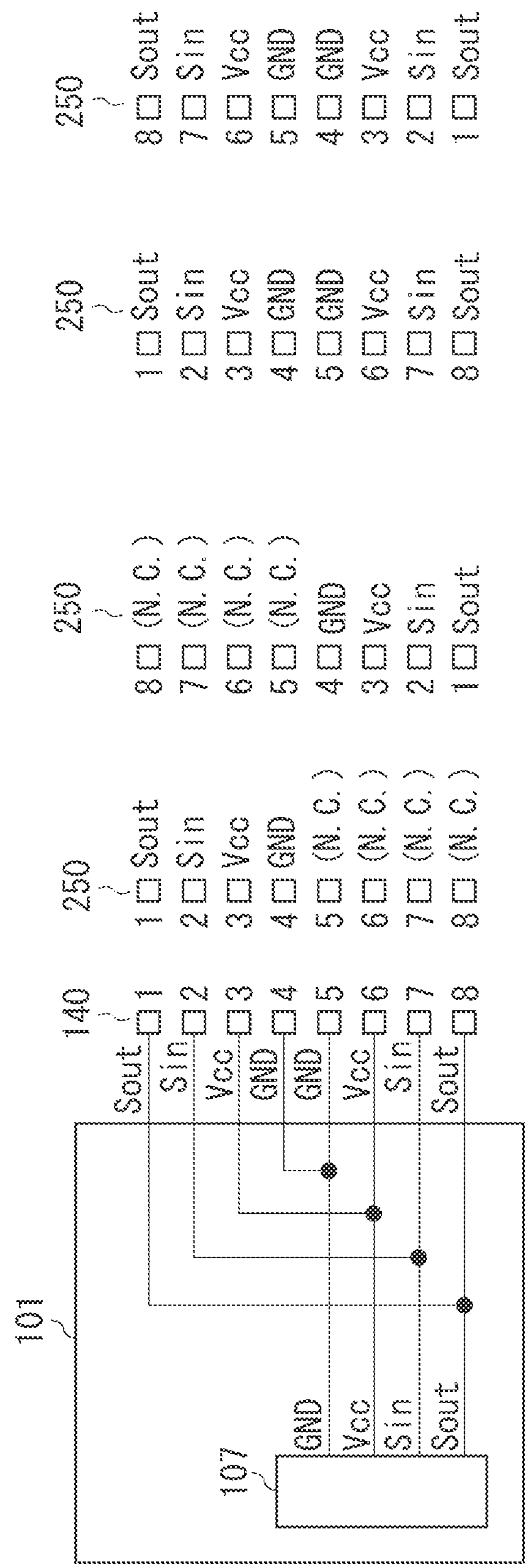

Pin assignments of the connection terminals 140 and 250 for achieving the above-described plurality of attachment forms will be described below with reference to FIGS. 9A through 9F. FIG. 9A illustrates pin assignments of the connection terminals 140 and 250 when both the connection terminals 140 and 250 include power supply lines and single-ended signal communication lines. Referring to FIG. 9A, pin assignments of the connection terminals 140 of the radiation imaging apparatus 100 are illustrated on the left-hand side, pin assignments of the connection terminals 250 of the connector 200 attached in the first attachment form are illustrated at the center, and pin assignments of the connection terminals 250 of the connector 200 attached in the second attachment form are illustrated on the right-hand side. These pin assignments are illustrated in association with each other. The connection terminals 140 protrude from the housing 101 of the radiation imaging apparatus 100, and the connection terminals 140 are connected to the wiring 107. The connection terminals 140 have pin Nos. 1 to 8 that are aligned in this order. Pin Nos. 1 and 8 correspond to the transmit signal Sout, pin Nos. 2 and 7 correspond to the receive signal Sin, pin Nos. 3 and 6 correspond to the power voltage Vcc, and pin Nos. 4 and 5 correspond to the reference potential GND. Pin Nos. 1 and 8, pin Nos. 2 and 7, pin Nos. 3 and 6, and pin Nos. 4 and 5 are respectively connected inside the connector 200. The connection terminals 250 include pin No. 1 corresponding to the transmit signal Sout, pin No. 2 corresponding to the receive signal Sin, pin No. 3 corresponding to the power voltage Vcc, pin No. 4 corresponding to the reference potential GND, and pin Nos. 5 to 8 normally closed (N.C.). Thus, since the pin assignments have point symmetry with respect to the center, a normal power supply path and a normal signal communication path are ensured even if the connector 200 is fit reversely. FIG. 9B illustrates an example of pin assignments of the connection terminals 250 when both the terminals 250 and 140 are arranged in point symmetry similar to the connection terminals 140 in the example illustrated in FIG. 9A. This example naturally allows reverse connection of the connector 200.

Figure 9C:
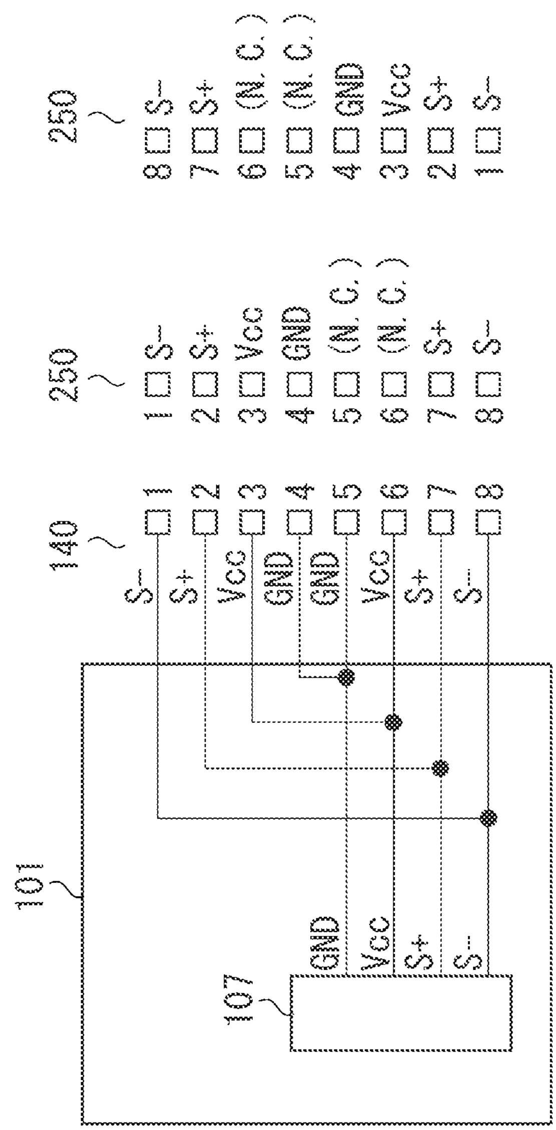

FIG. 9C illustrates an example of pin assignments of the connection terminals 140 and 250 in a case where power supply lines and differential signal communication lines are provided. The connection terminals 140 include pin Nos. 1 and 8 corresponding to the signal S−, pin Nos. 2 and 7 corresponding to the signal S+, pin Nos. 3 and 6 corresponding to the power voltage Vcc, and pin Nos. 4 and 5 corresponding to the reference voltage GND. On the other hand, the connection terminals 250 include pin Nos. 1 and 8 corresponding to the signal S−, pin Nos. 2 and 7 corresponding to the signal S+, pin No. 3 corresponding to the power voltage Vcc, pin No. 4 corresponding to the reference voltage GND, and pin Nos. 5 and 6 normally closed (N.C.). The above-described pin assignments enable reverse connection of the connector 200 even in a case where differential signals are used.

Figure 9D:
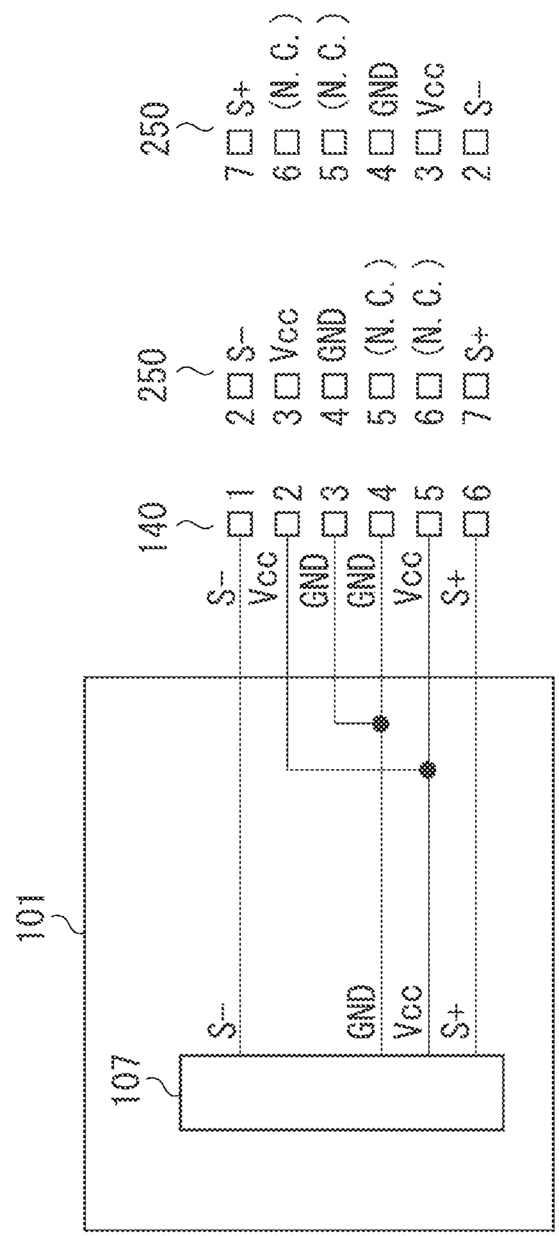

FIG. 9D illustrates an example of pin assignments of the connection terminals 140 and 250 including pin Nos. 1 to 6, which are aligned in this order. The connection terminals 140 include pin No. 1 corresponding to the signal S−, pin Nos. 2 and 5 corresponding to the power voltage Vcc, pin Nos. 3 and No. 4 corresponding to the reference voltage GND, and pin No. 6 corresponding to the signal S+. The connection terminals 250 include pin No. 2 corresponding to the signal S−, pin No. 3 corresponding to the power voltage Vcc, pin No. 4 corresponding to the reference voltage GND, and pin No. 7 corresponding to the signal S+. This configuration can reduce the number of pins, thereby reducing the size of the connector 200. In this case, when the connector 200 is connected reversely, the signal S− is applied to the signal line of the signal S+, and the signal S+ is applied to the signal line of the signal S−. Therefore, polarity determination processing and bit inversion processing are required.

Figure 9E:
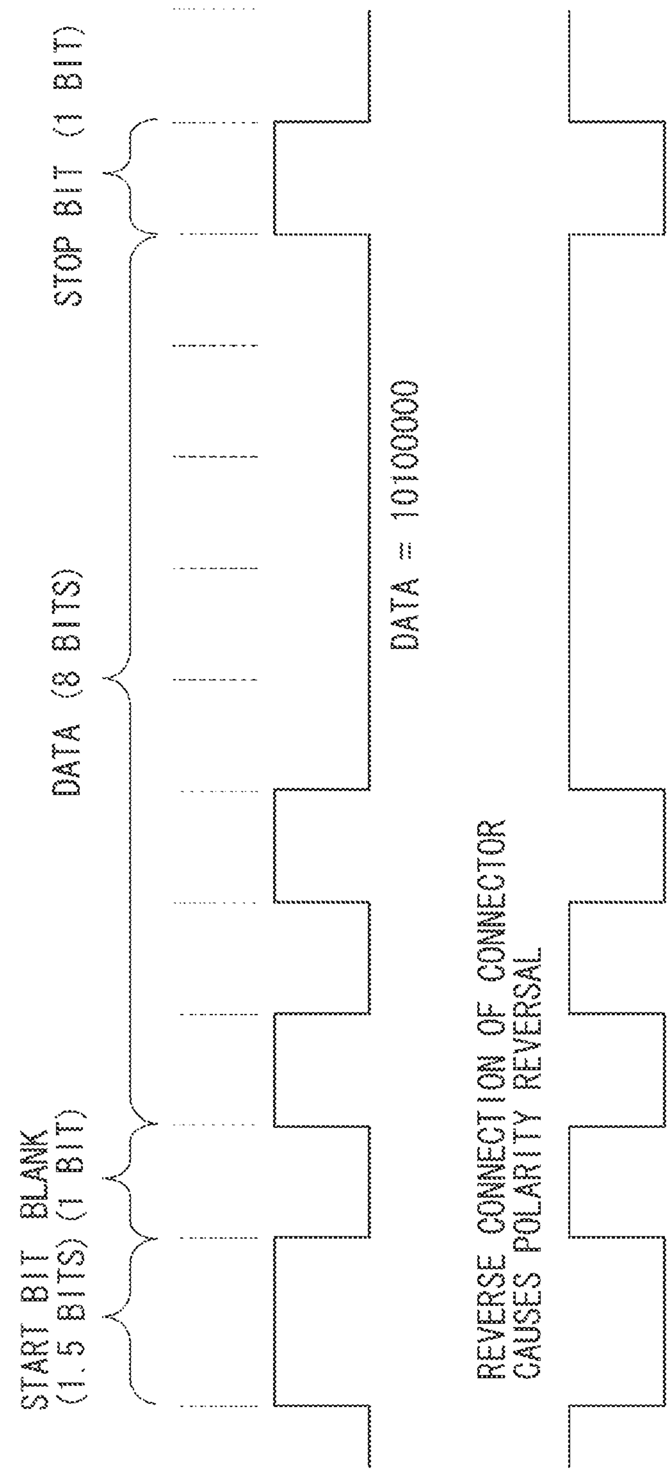

Polarity determination processing and bit inversion processing will be described below with reference to FIG. 9E. In particular, polarity reversal processing in the case of the asynchronous method will be described below. FIG. 9E illustrates an example of a signal in the case of the asynchronous method. The top illustrates input data "10100000" for the connection terminals 140. The input data includes 1.5-bit start bit, 1-bit blank, 8-bit data, and 1-bit stop bit. The bottom illustrates data when the data illustrated at the top is inverted.

In the case of the asynchronous method, the start bit precedes data bits. The start bit has a different bit length (1.5 bits) so as to be clearly distinguished from the data and other bits. When the receiving side, for example, the wired communication circuit of the radiation imaging apparatus 100, detects an edge of the signal with the 1.5-bit length, the wired communication circuit determines it as the start bit, and performs processing for receiving the subsequent data. In this case, the wired communication circuit detects the polarity of the signal when the start bit is detected. In the above-described example, when the start bit is "H", it is determined that the connector 200 is connected with normal polarity (normal fitting or the first attachment form). When the start bit is "L", it is determined that the connector 200 is connected with reverse polarity (reverse fitting or the second attachment form). When the determination result is reverse polarity, the wired communication circuit performs processing for either reversing the polarity of the received signal to receive data, or collectively inverting the data bits after 8-bit data has been received, so that the receiving side can normally receive data transmitted from the transmitting side.

Figure 9F:
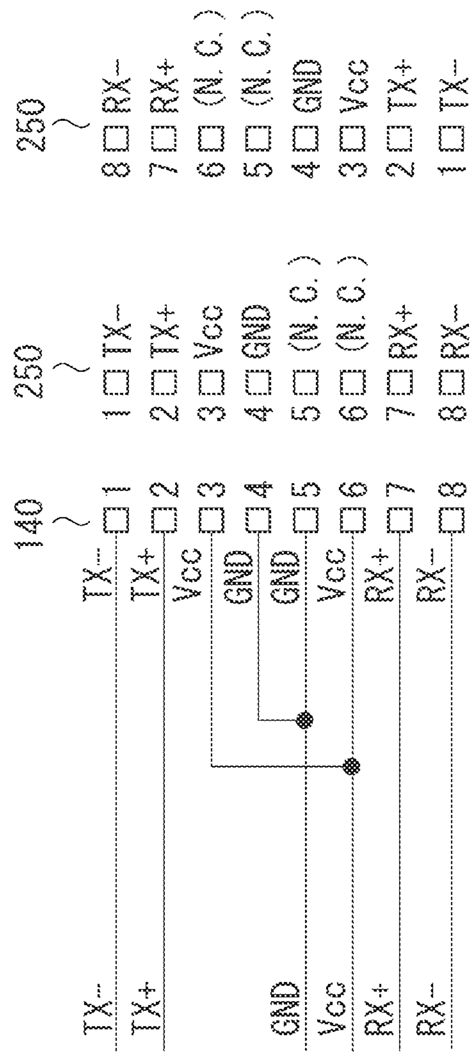

In the example illustrated in FIG. 9F, the connection terminals 140 include pin No. 1 corresponding to the transmitting side signal TX−, pin No. 2 corresponding to the transmitting side signal TX+, pin Nos. 3 and 6 corresponding to the power voltage Vcc, pin Nos. 4 and 5 corresponding to the reference voltage GND, pin No. 7 corresponding to the receiving side signal RX+, and pin No. 8 corresponding to the receiving side signal RX−. The connection terminals 250 include pin Nos. 1 to 4, 7, and 8 assigned in a similar way to the connection terminal 140, and pin Nos. 5 and 6 normally closed (N.C.). With these pin assignments, since in-phase transmit and receive signal lines are arranged in point symmetry, transmit and receive signals are reversed on the receiving side when the connector 200 is connected reversely (a signal polarity determination is not performed). In this case, the receiving side apparatus performs processing for reversing connection destinations of the transmit and receive signals. This function is referred to as automatic crossover function. Auto-medium dependent interface crossover (Auto-MDIX) for Ethernet (registered trademark) is a typical automatic crossover function. Auto-MDIX is standardized in Article 40.4.4 of Institute of Electrical and Electronics Engineers (IEEE) 802.3.

Figure 10:
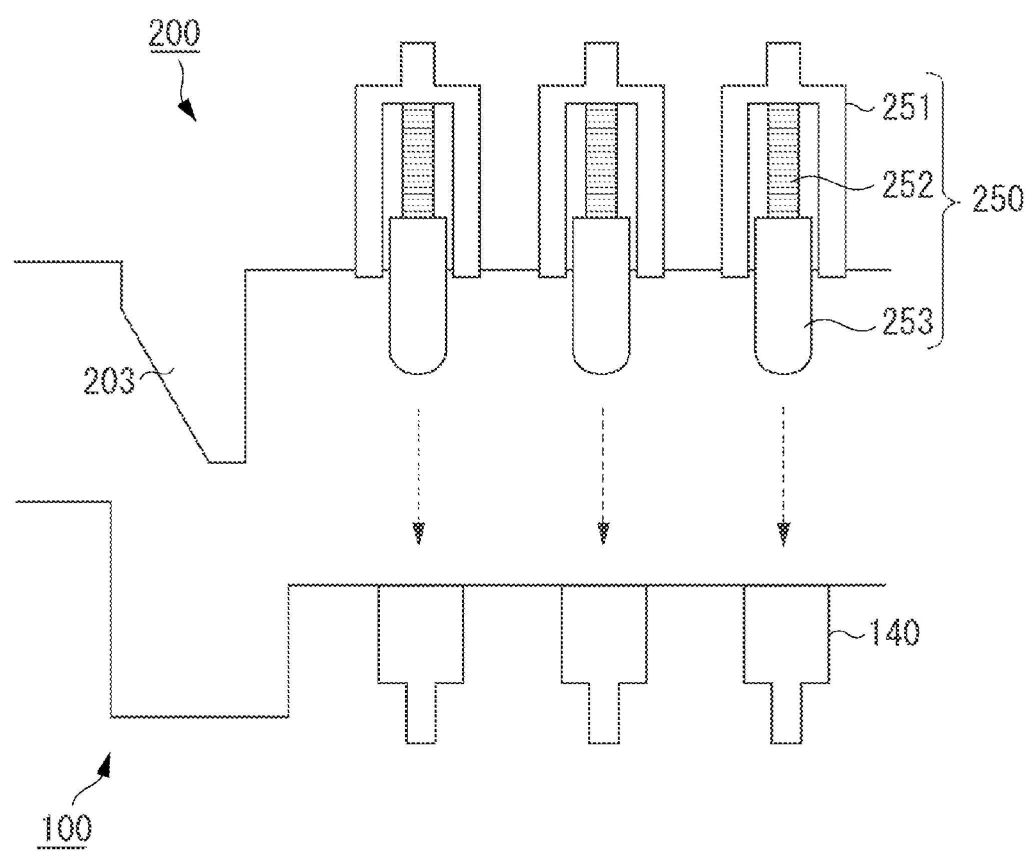
FIG. 10 illustrates electrical connection portions of the radiation imaging apparatus and the connector according to an exemplary embodiment.

The configuration of the connector-side connection terminals 250 and the apparatus-side connection terminals 140 according to an exemplary embodiment will be described below with reference to FIG. 10. Each of the connection terminals 250 is a spring probe composed of two parts (a spring 252 and a plunger 253 or three parts (a spring 252, a plunger 253, and a barrel 251). The barrel 251 is fixed inside the connector 200, and is connected to each electric wire of the cable 300. The spring 252 is an elastic member for applying outward pressure to the plunger 253. In the barrel 251, the plunger 253 is movable perpendicularly to the connection surface for connection with the radiation imaging apparatus 100, and is retained while being outwardly pressed by the spring 252. On the other hand, each of the connection terminals 140 has a simple pin structure having a flat surface portion for connection with the plunger 253. When the connector 200 is fixed to the radiation imaging apparatus 100, the spring 252 presses the plunger 253 against the flat surface portion of each connection terminal 140, allowing connection between the radiation imaging apparatus 100 and the cable 300. Using a connection method for general connectors, such as fitting each terminal, may damage the connection portion. However, the above-described configuration can prevent damage to the connection portion even if the connector 200 is detached from the radiation imaging apparatus 100 by overload. The spring probe is larger in size than the simple pin structure. To minimize the increase in size of the radiation imaging apparatus 100, it is desirable that the connection terminals 140 in the radiation imaging apparatus 100 has a simple pin structure, and that the connection terminals 250 in the connector 200 are spring probes. Providing the outer wall portion 203 to surround the connection terminals 250, and further providing a taper to the outer wall portion 203 enable each spring probe to be insusceptible to lateral external loads. The outer wall portion 203 can also function as a guide for attaching the connector 200.

Figure 11A:
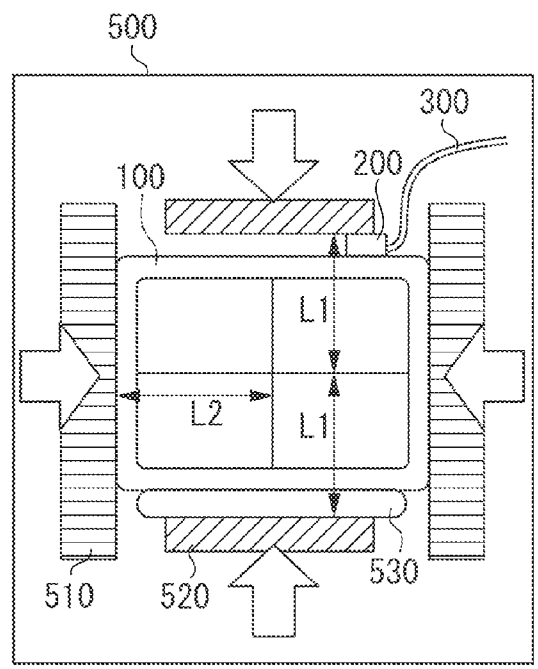
FIGS. 11A and 11B illustrate a storage portion for storing the radiation imaging apparatus according to an exemplary embodiment.
Figure 11B:
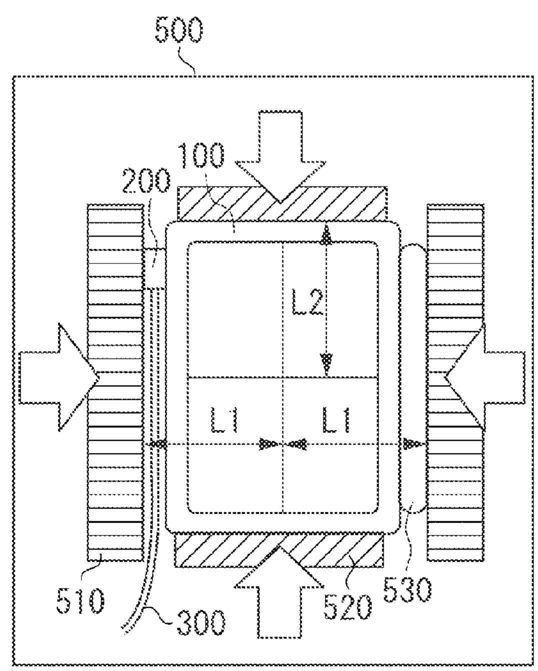

FIGS. 11A and 11B illustrate two usage forms in which the radiation imaging apparatus 100 is stored in a storage portion 500 of a rack, such as an imaging table. The storage portion 500 includes two positioning mechanisms 510 movable in the horizontal direction, each moving in an interlocked manner. Likewise, the storage portion 500 further includes two positioning mechanisms 520 movable in the vertical direction. Generally, the storage portion 500 is designed for the standard size (384×460 mm) of a conventional film cassette having a 14×17-inch image effective area.

Since the film cassette may be rotated by 90 degrees, the maximum outer shape of a mounting area formed by the positioning mechanisms 510 and 520 is a squire having a side length of 460 mm. The positioning mechanisms 510 and 520 move to form a mounting area according to an imaging apparatus to be mounted. For an imaging apparatus having a vertically and horizontally symmetric shape, such as a conventional film cassette, the movement of the positioning mechanisms 510 and 520 enable the center of the storage portion 500 and the center of the imaging apparatus stored therein to match each other.

For the radiation imaging apparatus 100 having the connector 200, positioning of the center is also possible by using similar positioning mechanisms having the following configuration. An outermost distance L1 indicates the distance from the center of the X-ray reading area of the radiation imaging apparatus 100 to the outer edge of the connector 200, and a distance L2 indicates the distance from the center of the X-ray reading area to the side surface orthogonal to the side surface to which the connector 200 is connected. The distances L1 and L2 are formed so that a relation $L1 \leq L2$ is satisfied. Here, the outer edge of the connector 200 refers to the side surface disposed at a position most away from the side surface of the radiation imaging apparatus 100 when the connector 200 is attached to the radiation imaging apparatus 100. In an exemplary embodiment, the outer edge of the connector 200 is a surface in parallel with the side surface of the radiation imaging apparatus 100, and is different from the contact surface. Specifically, the distance L2 is designed to be about 230 mm (=460×½) based on the standard size of a conventional film cassette. The distance L1 is designed to be a half or less (about 230 mm or less) of the maximum outer shape of the positioning mechanisms 510 and 520. In addition, a spacer 530 is disposed on the side opposite to the connector 200 so that an outermost distance from the center of the X-ray reading area to the spacer 530 is L1. Thus, in the storage portion 500 for a conventional film cassette, it is also possible to match the center of the X-ray reading area of the radiation imaging apparatus 100 and the center of the storage portion 500.

As illustrated in FIGS. 11A and 11B, there are cases where the cable outlet 201 of the connector 200 is to be outwardly oriented (FIG. 11A) and inwardly oriented (FIG. 11B) depending on the usage form. Therefore, if the connector 200 functions in whichever orientation the connector 200 is attached, the operability can be improved. This is achieved, for example, by using the structure as illustrated in FIGS. 8A and 8B.

In another exemplary embodiment, a rotation mechanism for rotatably retaining the storage portion 500 around the normal line of the X-ray sensor panel 103, i.e., with respect to the X-ray incidence direction is provided, and the radiation imaging apparatus 100 is retained by a retaining member including the storage portion 500 and the rotation mechanism. Thus, the radiation imaging apparatus 100 enables both vertical imaging (portrait imaging) and horizontal imaging (landscape imaging).

The time and effort for attaching the connector 200 can be efficiently saved if the connector 200 is fixed to the storage portion 500, and the connector 200 and the radiation imaging apparatus 100 are connected to each other when the radiation imaging apparatus 100 is stored in the storage portion 500.

Figure 12:
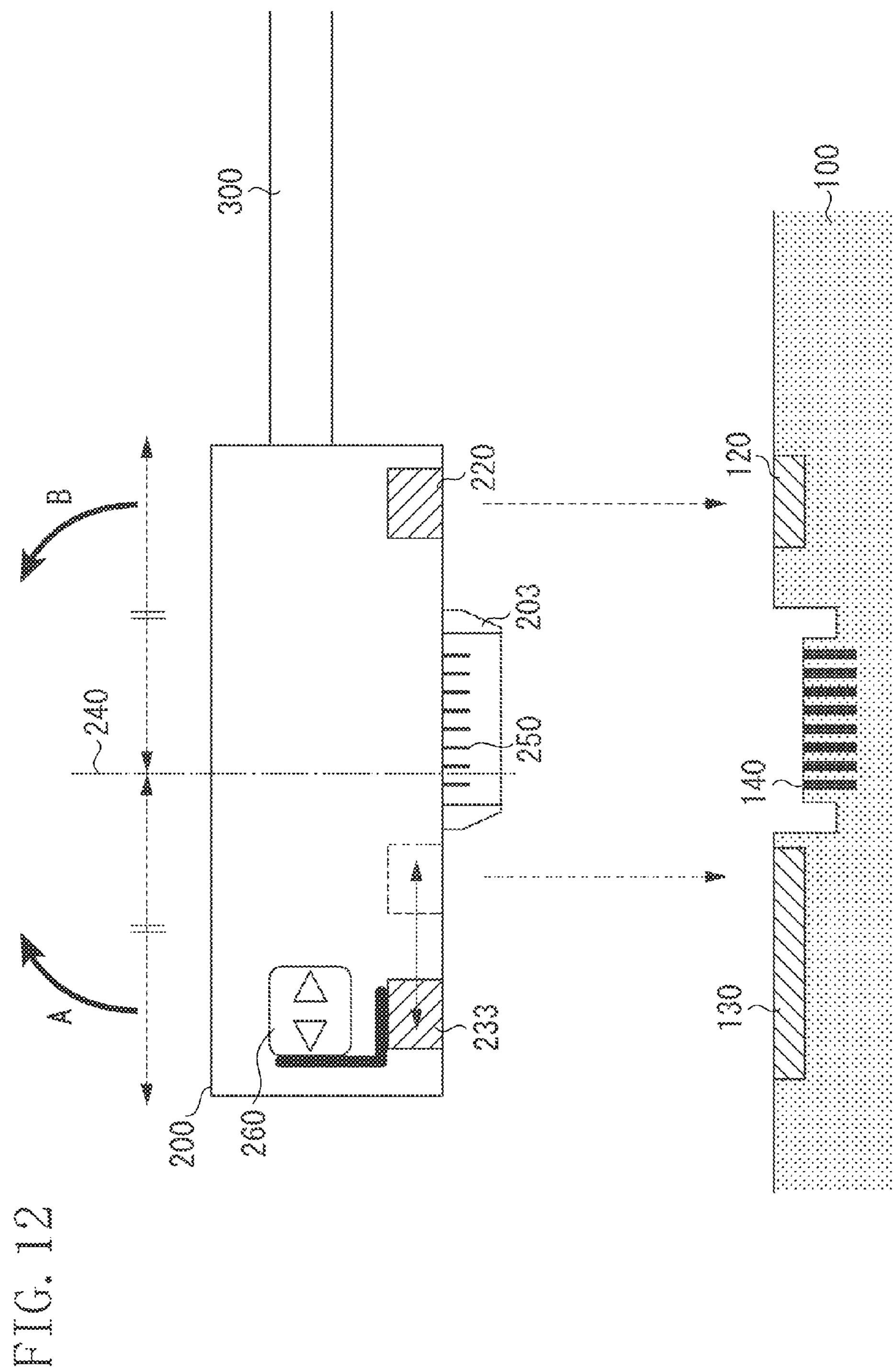
FIG. 12 illustrates a connector according to an exemplary embodiment in which the position of a connector-side fixing member is adjustable.

FIG. 12 illustrates a connector according to an exemplary embodiment. A connector 200 is provided with an adjustment member for adjusting the magnitude of the moment to be applied to the connector 200 according to an exemplary embodiment. As described in the above-described exemplary embodiments, the connection retaining force and the force required to detach the connector 200 can be adjusted by the magnetic attraction forces, the magnet positions, and the cable outlet position. However, the force with which each operator feels it easy to detach the connector 200 may be different depending on the muscle force, the hand size, and the like of the operator. In the present exemplary embodiment, the connector 200 is provided with a sliding switch 260. The switch 260 is connected to a magnet 233, and moving the switch 260 to move the position of the magnet 233 can change the distance from the magnet 233 to the connector outline center axis 240. This can adjust the moment of force required to detach the connector 200 in the direction A to be adjusted, allowing the operator to freely adjust the operation feeling.

Figure 13:
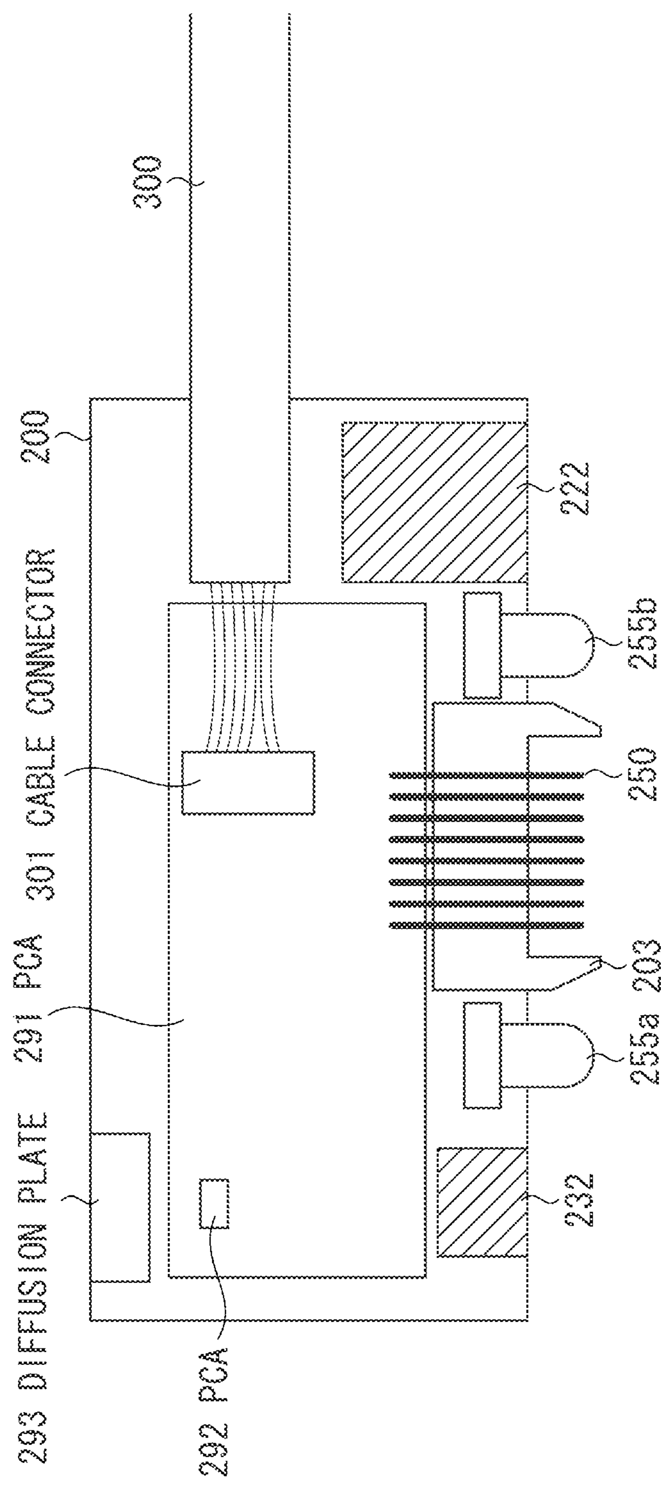
FIG. 13 illustrates an internal structure of the connector according to an exemplary embodiment.

The internal structure of the connector 200 according to an exemplary embodiment will be described below with reference to FIG. 13. Duplicated descriptions of the above-described configuration will be omitted. The connector 200 includes a printed circuit assembly (PCA) 291, a light emitting diode (LED) 292, which is connected onto a printed circuit board, a diffusion plate 293, and a cable connector 301 for connecting the PCA 291 and the cable 300. The cable 300 is fixed to the connector housing 210. A part of, for example, 15 signal lines taken out from the cable 300 are connected to the first surface of the PCA 291, and the remaining signal lines are connected to the second surface of the PCA 291. The PCA 291 is fixed to the connector housing 210 and is soldered to the connection terminals 250. The PCA 291 transmits the power and signals supplied from the cable 300 to the connection terminals 250. The PCA 291 further receives signals from the radiation imaging apparatus 100, and controls the lighting state of the LED 292 based on these signals.

The LED 292 turns on under the control of the PCA 291. The diffusion plate 293 diffuses light emitted from the LED 292. Since the cable 300 is connected to the connection terminals 250 via the PCA 291, the cable 300 is not directly connected to the pins, facilitating replacement and repair of the cable 300 when damaged.

The LED 292 is controlled in the following four (first to fourth) modes by the PCA 291 based on the signals received from the radiation imaging apparatus 100. The first mode, in which the LED 292 is continuously turned on, is executed when the battery of the radiation imaging apparatus 100 is fully charged, or when the battery has been fully charged by the power from the cable 300. The second mode, in which the LED 292 repetitively blinks at first time intervals, is executed when the battery of the radiation imaging apparatus 100 is being charged by the power from the cable 300. The third mode, in which the LED 292 repetitively blinks at second time intervals shorter than the first time intervals, is executed when the power being supplied to the radiation imaging apparatus 100 has some problem. The fourth mode, in which the LED 292 is off, indicates the battery is not being charged.

The LED 292 is not limited to the above-described example. The LED 292 may display the statuses of the power supply and the communication path under the control of the PCA 291. When the cable 300 is connected only to the control apparatus 410, the LED 292 may display the status of the communication path. Information about the communication path includes, for example, whether data is being transmitted or received, whether an error has occurred in the communication path, and whether the quality of communication is high or low. These examples can be also achieved by monitoring the status of the radiation imaging apparatus 100 or monitoring the signals from the cable 300 or the connection terminals 140 via the PCA 291, and controlling the display of the LED 292 according to the result of the monitoring.

Although, in the above-described exemplary embodiments, the connector 200 includes magnets as fixing members, the configuration according to the present invention is not limited thereto. The radiation imaging apparatus 100 may include magnets, or the connector 200 may include a latch mechanism capable of being detached by a detachment load.

In addition, any suitable combinations of the above-described exemplary embodiments are also included in exemplary embodiments of the present invention.

According to the above-described exemplary embodiments, it is possible to provide a structure for cable connection to the radiation imaging apparatus, which ensures a sufficient force for retaining the connection when the cable is pulled and prevents the operability from being degraded when detaching the cable. Further, for cable connection to the radiation imaging apparatus using magnets, it is possible to set a large magnetic attraction force so that the cable cannot be detached during routine operations such as the routing of a cable and the movement of an X-ray imaging apparatus and can be detached only if a load strong enough to damage the X-ray imaging apparatus or the cable is applied. This can reduce the possibility of the operability being degraded because the cable connection using magnetic attraction becomes easily detached in an unintended way by vibrations, the cable's own weight and the like, and can further reduce failures in the radiation imaging system and the X-ray imaging apparatus.

As described above, for cable connection to the radiation imaging apparatus, it is possible to ensure both a sufficient force for retaining the connection when the cable is pulled, and the operability when detaching the cable.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-044403 filed Mar. 6, 2013, which is hereby incorporated by reference herein in its entirety.

What is claimed is:

1. A radiation imaging system having a connector for connection to an external apparatus, and a radiation imaging apparatus to which the connector is detachably attached wherein the radiation imaging apparatus includes
- a radiation sensor;
- a housing configured to store the radiation sensor;
- an apparatus-side connection terminal provided on a side surface of the housing; and
- an apparatus-side fixing member, and wherein the connector includes
- a connector-side connection terminal configured to be connected to the apparatus-side connection terminal;
- a first connector-side fixing member configured to produce a predetermined fixing force with the apparatus-side fixing member;
- a second connector-side fixing member configured to produce a fixing force with the apparatus-side fixing member, wherein the fixing force produced by the second connector-side fixing member is greater than the predetermined fixing force produced by the first connector-side fixing member, and an outlet of a cable configured to connect the radiation imaging apparatus to the external apparatus, the outlet being disposed at a position closer to the second connector-side fixing member than to the first connector-side fixing member.

2. The radiation imaging system according to claim 1, wherein, at two longitudinal ends including a first end and a second end of a connection surface of the connector, a magnitude of moment produced around the second end by the first and second connector-side fixing members is larger than a magnitude of moment produced around the first end by the first and second connector-side fixing members.

3. The radiation imaging system according to claim 1, wherein a magnitude of moment produced around a center axis of the connector by the second connector-side fixing member is larger than the magnitude of the moment produced around the center axis of the connector by the first connector-side fixing member.

4. The radiation imaging system according to claim 1, wherein at least either the first and second connector-side fixing members or the apparatus-side fixing member are provided with magnets having different magnetic forces.

5. The radiation imaging system according to claim 1, wherein, when the connector is connected to the radiation imaging apparatus by using magnets as the first and second connector-side fixing members, the magnets are arranged to have the same polarities on a surface side along the apparatus-side fixing member.

6. The radiation imaging system according to claim 1, wherein the apparatus-side fixing member is made of a plate member that forms contact surfaces for mutually producing fixing forces with the first and second connector-side fixing members, and has a hole into which the connector-side connection terminals are inserted.

7. The radiation imaging system according to claim 6, wherein the connector further includes a protruding member at least one of between the connector-side connection terminals and the first connector-side fixing member and between the connector-side connection terminals and the second connector-side fixing member, and wherein the plate member further includes a hole portion into which the protruding member is inserted.

8. The radiation imaging system according to claim 1, wherein the connector further comprises a protruding member at least one of between the connector-side connection terminals and the first connector-side fixing member and between the connector-side connection terminals and the second connector-side fixing member.

9. The radiation imaging system according to claim 1, wherein the connector includes a first side and a second side different from the first side, wherein the first connector-side fixing member, the connector-side connection terminal and the second connector-side fixing member are disposed on the first side, and wherein the connector further comprises a recessed portion allowing the connector to be held, the recessed portion being disposed on the second side and at a position closer to the first connector-side fixing member than to the second connector-side fixing member.

10. The radiation imaging system according to claim 1, wherein a first attachment form for attaching the connector to the radiation imaging apparatus, and a second attachment form for attaching the connector to the radiation imaging apparatus in an orientation reverse to the orientation of the connector in the first attachment form are provided by the first and second connector-side fixing members, a first apparatus-side fixing member and a second apparatus-side fixing member, the apparatus-side connection terminals, and the connector-side connection terminals.

11. The radiation imaging system according to claim 10, wherein a first attachment form for connecting the connector-side connection terminals and the apparatus-side connection terminals by a fixing force produced by a pair of the first connector-side fixing member and a first area of the first apparatus-side fixing member and a fixing force produced by a pair of the second connector-side fixing member and a second area of the second apparatus-side fixing member, and a second attachment form for connecting the connector-side connection terminals and the apparatus-side connection terminals by a fixing force produced by a pair of the first connector-side fixing member and the second area and a fixing force produced by a pair of the second connector-side fixing member and the first area are provided.

12. The radiation imaging system according to claim 10, wherein a magnitude of sum of moments exerted on the connector by the first and second connector-side fixing members is substantially identical in the first and second attachment forms.

13. The radiation imaging system according to claim 10, wherein respective pin assignments on the connector-side connection terminals and the apparatus-side connection terminals are symmetric.

14. The radiation imaging system according to claim 1, wherein each of the connector-side connection terminals includes a protruding member in contact with one of the apparatus-side connection terminals, and an elastic member for applying outward pressure to the protruding member.

15. The radiation imaging system according to claim 1, wherein an outermost distance from a center of a reading area of the radiation imaging apparatus to an outer edge of the connector is equal to or less than a distance from the center of the reading area to a side surface orthogonal to a side surface to which the connector is connected.

16. The radiation imaging system according to claim 1, further comprising a retaining member of the radiation imaging apparatus configured to rotate around a normal line of the radiation sensor, wherein the connector is fixed to a position where the connector and the radiation imaging apparatus becomes connected to each other when the radiation imaging apparatus is stored in the retaining member.

17. The radiation imaging system according to claim 1, further comprising an adjustment unit configured to adjust a magnitude of moment to be applied to the connector by at least one of the first and second connector-side fixing members.

18. The radiation imaging system according to claim 17, wherein the adjustment unit is a member for changing a position of at least one of the first and second connector-side fixing members.

19. The radiation imaging system according to claim 1, wherein, when a force larger than a predetermined force is applied to the connector in a direction away from the radiation imaging apparatus in a state where the connector is attached to the radiation imaging apparatus by the first and second apparatus side fixing members, the connector becomes detached from the radiation imaging apparatus.

20. The radiation imaging system according to claim 1, further comprising a display unit configured to display a status of at least one of the communication path and the power that are provided to the radiation imaging apparatus by the connector.

21. The radiation imaging system according to claim 1, further comprising an image display terminal comprising a reception unit configured to receive radiation image data obtained by the radiation sensor from the radiation imaging apparatus, and a transmission unit configured to transmit control signals to the radiation imaging apparatus.

22. The radiation imaging system according to claim 1, further comprising a radiation generation apparatus configured to irradiate the radiation sensor with radiation.

23. A connector, detachable to a partner apparatus, to be connected to an end of a cable for providing the partner apparatus with at least one of power and a communication path, the connector comprising:

a connector-side connection terminal configured to be connected to a connection terminal of the partner apparatus;

a first connector-side fixing member configured to mutually produce a predetermined fixing force with a first area of the partner apparatus;

a second connector-side fixing member configured to mutually produce a fixing force larger than the predetermined fixing force with a second area of the partner apparatus; and an outlet of a cable configured to connect the connector to the partner apparatus, the outlet being disposed at a position closer to the second connector-side fixing member than to the first connector-side fixing member.

24. The radiation imaging system according to claim 1, wherein the first connector-side fixing member, the connector-side connection terminal and the second connector-side fixing member are disposed on a first side of the connector, and wherein the outlet is disposed on a side different from the first side.

25. The connector according to claim 23, wherein the connector includes a first side and a second side different from the first side, wherein the first connector-side fixing member, the connector-side connection terminal and the second connector-side fixing member are disposed on the first side, and wherein the outlet is disposed on the second side.

* * * * *